US011839296B2

(12) United States Patent
Davenport et al.

(10) Patent No.: US 11,839,296 B2
(45) Date of Patent: Dec. 12, 2023

(54) DEVICES FOR SUPPORTING A PATIENT'S EXTREMITIES

(71) Applicant: Ghroov LLC, New Berlin, WI (US)

(72) Inventors: Mary Davenport, Brookfield, WI (US); Courtney Voden, New Berlin, WI (US); Blake Gray, Kihei, HI (US); Mark Gondek, Milwaukee, WI (US); Joshua McKune, Milwaukee, WI (US); Carl Dekker, Sugar Grove, IL (US); Charlie Richard, Sugar Grove, IL (US); Dave Gerow, Milwaukee, WI (US)

(73) Assignee: Ghroov LLC, New Berlin, WI (US)

( * ) Notice: Subject to any disclaimer, the term of this patent is extended or adjusted under 35 U.S.C. 154(b) by 843 days.

(21) Appl. No.: 16/529,713

(22) Filed: Aug. 1, 2019

(65) Prior Publication Data
US 2020/0037752 A1 Feb. 6, 2020

Related U.S. Application Data

(60) Provisional application No. 62/713,896, filed on Aug. 2, 2018.

(51) Int. Cl.
F16M 11/00 (2006.01)
A47B 3/02 (2006.01)
(Continued)

(52) U.S. Cl.
CPC ............... A47B 3/02 (2013.01); A47B 3/08 (2013.01); A47C 7/506 (2013.01); A61B 6/0407 (2013.01); A61G 5/125 (2016.11); A61G 5/127 (2016.11)

(58) Field of Classification Search
CPC .. A47B 3/08; A47B 3/02; A47G 7/506; A61B 6/0407
See application file for complete search history.

(56) References Cited

U.S. PATENT DOCUMENTS 591,099 A * 10/1897 Harbaugh ............ A47C 20/027
5/634
1,296,722 A 3/1919 Washburn
(Continued)

FOREIGN PATENT DOCUMENTS

CN 200963323 Y 10/2007
CN 202376354 U 8/2012
(Continued)

OTHER PUBLICATIONS

Benmore Medical (UK) Limited, "Adjustable Limb Support", webpage, 2018, available at https://www.penmormedical.co.uk/product/adjustable-limb-support/.
(Continued)

Primary Examiner — Amy J. Sterling
(74) Attorney, Agent, or Firm — Andrus Intellectual Property Law, LLP

(57) ABSTRACT

A device for supporting a person's extremities includes a first arm, a second arm pivotably coupled to the first arm, and an appendage support coupled to the first and second arms. The device is configurable in a use position, in which the appendage support is not parallel to at least one of the first and second arms while remaining coupled to the first and second arms. The device is also configurable in a collapsed position, in which the first and second arms and the appendage support are generally parallel to one another while remaining coupled to one another.

10 Claims, 23 Drawing Sheets

(51) Int. Cl.
*A61B 6/04* (2006.01)
*A47C 7/50* (2006.01)
*A47B 3/08* (2006.01)
*A61G 5/12* (2006.01)

(56) References Cited

U.S. PATENT DOCUMENTS

| | | | | |
|---|---|---|---|---|
| 2,346,722 | A * | 4/1944 | Lura | A47C 20/021 5/648 |
| 2,581,110 | A * | 1/1952 | Kenworthy | A61G 7/0755 5/651 |
| 3,065,992 | A * | 11/1962 | Nagel | B60N 3/063 297/423.46 |
| 3,066,322 | A | 12/1962 | Derby | |
| 4,471,768 | A * | 9/1984 | Ciullo | A61B 17/58 606/86 R |
| 6,295,987 | B1 | 10/2001 | Parker et al. | |
| 6,962,570 | B2 * | 11/2005 | Callanan | A61H 1/024 601/5 |
| 8,322,342 | B2 * | 12/2012 | Soto | A61G 13/12 128/845 |
| 8,485,952 | B2 | 7/2013 | Gehrke | |
| 8,572,781 | B2 * | 11/2013 | Schlanger | A61F 5/3761 5/648 |
| 9,056,042 | B2 * | 6/2015 | Russell | A61G 13/124 |
| 11,395,680 | B2 * | 7/2022 | Chen | A61B 17/8866 |
| 2002/0128577 | A1 * | 9/2002 | Smart | A61G 13/12 602/32 |
| 2003/0078144 | A1 * | 4/2003 | Gehrke | A47C 20/021 482/140 |
| 2006/0272893 | A1 | 12/2006 | Foggio et al. | |

FOREIGN PATENT DOCUMENTS

| | | |
|---|---|---|
| CN | 203138947 U | 8/2013 |
| CN | 203815772 U | 9/2014 |
| CN | 203874036 U | 10/2014 |
| CN | 204542671 U | 8/2015 |
| CN | 205322679 U | 6/2016 |

OTHER PUBLICATIONS

Carbonlite Medical Technology, "Cambridge Portable Limb Support", webpage, 2018, available at https://cdn.shopify.com/s/files/1/1800/0103/products/cam3_1024x1024.jpg?v=1497221198.

Immoclinc, "Armrest / height-adjustable 22100 Immoclinc", webpage, at least as early as Mar. 2018, image available at http://img.medicalexpo.com/images_me/photo-g/68863-8028228.jpg.

Mizuho Osi, "Adjustable Leg Rest", webpage, 2018, available at https://www.mizuhosi.com/products/accessories/lower-extremity-positioning/adjustable-leg-rest/, accessed Apr. 13, 2018.

Provita Medical, "Armrest / height-adjustable S1112007 Provita Medical", webpage, 2018, available at http://www.medicalexpo.com/prod/provita-medical/product-69770-590339.html, accessed Mar. 27, 2018.

Rock West Composites, "Push Button Ratchet Joint—198 Degrees / 18 Deg Increment—0.75 Inch Tube", webpage, 2022, available at https://www.rockwestcomposites.com/shop/connector-accessories/other-joints/push-button-ratchet-joints/464090?srsltid=AYJSbAeICP0MbtFdrjppk2nH6ETLJYNdxtLe9juBhTkYcYRI28qCiw-S9VU, accessed Dec. 20, 2022.

* cited by examiner

DEVICES FOR SUPPORTING A PATIENT'S EXTREMITIES

CROSS-REFERENCE TO RELATED APPLICATION

The present application claims the benefit of U.S. Provisional Application Ser. No. 62/713,896, filed Aug. 2, 2018, which is hereby incorporated by reference herein in its entirety.

FIELD

The present disclosure relates to devices for supporting a patient's extremities, such as, but not limited to, arms, legs, and head, while a dressing is being changed or a wound being cleaned on such extremity.

BACKGROUND

U.S. Pat. No. 1,296,722 discloses a leg rest for medical and surgical uses in treating and dressing a patient's limb.

U.S. Pat. No. 3,066,322 discloses a portable and collapsible leg and foot rest and more particularly an improved leg rest adapted for use by a person in a reclining position to elevate one or both legs and to which may be attached a foot support adapted to immobilize the patient's foot in any required position for beneficial therapy in cases of infantile paralysis or other disease or injury.

U.S. Pat. No. 6,295,987 discloses a medical limb rest for elevating a body appendage including sterilized components. The sterilized components can comprise a support tray having a top surface and an underside. The top surface of the support tray forms a concave section. Preferably, the support tray can have a first edge, a second edge opposite the first edge, and two side edges. The first edge is curved towards the underside to define a first groove and the second edge is curved toward the underside to define a second groove. Other components of the medical limb rest comprise at least two pairs of legs, a first pair and a second pair. The first pair of legs includes a first leg pivotally connected to a second leg and the second pair of legs comprise a third leg pivotally connected to a forth leg. Each pair of pivotally connected legs is attached to another pair of pivotally connected legs by one or more trusses. A first truss connects the top end of the first leg to the top end of the third leg and a second truss connects the top end of the second leg to the top end of the fourth leg. Preferably, the trusses are precisionally machined to snugly fit within the grooves. The supporting legs of the limb rest can also comprise a set of one piece frames.

U.S. Pat. No. 8,485,952 discloses a leg elevator. The leg elevator includes a base having a lower leg end and an upper leg end, a portion of the base having at least one support retaining device. A lower leg support is provided. A height adjustment mechanism is also provided having a support leg pivotally attached at a first end to the lower leg support. The support leg has a second end attached to a support bar extending perpendicular to the support leg. The support bar is removably engaged with the at least one support retaining device such that a height of the lower leg support above the base may be adjusted. An upper leg adjustment mechanism is operably connected to the upper leg end of the base for adjusting a distance between the upper leg end of the base and the lower leg support. An upper leg support is operably attached to the upper leg adjustment mechanism. An angle adjustment mechanism is provided between the upper leg adjustment mechanism and the lower leg support for adjusting a relative angular orientation of the upper leg support relative to the lower leg support.

U.S. Patent Application Publication No. 2006/0272893 discloses an adjustable limb support device comprising a front lift and a rear lift, each disposed substantially beneath a top plate. A drive mechanism adapted to drive the front and rear lifts both concurrently and independently, thereby permitting the elevation of the top plate to be raised or lowered and permitting the top plate to tilt off a horizontal plane.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

According to one example of the present disclosure, a device for supporting a person's extremities includes a first arm, a second arm pivotably coupled to the first arm, and an appendage support coupled to the first and second arms. The device is configurable in a use position, in which the appendage support is not parallel to at least one of the first and second arms while remaining coupled to the first and second arms. The device is also configurable in a collapsed position, in which the first and second arms and the appendage support are generally parallel to one another while remaining coupled to one another.

According to another example of the present disclosure, a device for supporting a person's extremities includes an elongated base having a first end and a second end. An elongated appendage support has a first end and a second end, the first end of the appendage support being pivotably coupled to the base at the first end of the base. A locking arm is engageable with the appendage support and the base. The device is configurable in a use position, in which the second end of the appendage support is located a first distance from the second end of the base, and the appendage support is prevented from pivoting with respect to the base by way of engagement with the locking arm. The device is also configurable in a collapsed position, in which the second end of the appendage support is located at a second, shorter distance from the second end of the base, and the locking arm is sandwiched between the base and the appendage support.

BRIEF DESCRIPTION OF THE DRAWINGS

The present disclosure is described with reference to the following Figures. The same numbers are used throughout the Figures to reference like features and like components.

DETAILED DESCRIPTION

The following devices and assemblies are used for supporting a patient's extremities, such as his or her legs, arms, and/or head while a dressing is being changed and/or a wound is being cleaned on such extremity. The devices could be used in the fields of orthopedics, surgery, the ICU, long-term healthcare, military, EMT/paramedics, or anywhere where wound care is required. Generally, such wound care requires a lot of manpower if no device for supporting the patient's extremities is available. Specifically, a first person must support the patient's extremity while a second person changes the patient's dressing and cleans his or her wound. Ergonomics in such a situation are very poor. Several products exist that are supported from the ceiling above the patient's bed. However, not all hospitals or medical settings are equipped with such devices, which are expensive and which require time to install. Additionally, such products are not easily transportable to a patient. Free-standing products exist for supporting a patient's extremities; however, such products are either not easily or not completely collapsible, making them difficult to transport from one patient to another.

The designs according to the present disclosure increase productivity by requiring fewer medical personnel to attend to a patient's needs. They also provide ergonomic benefits to medical personnel. Because many of the designs according to the present disclosure are small, compact, collapsible, lightweight, and cost-effective, these designs (or portions thereof) can be used for a single patient, thereby preventing cross-contamination of a disease from patient to patient. The devices according to the present disclosure are laterally and/or vertically adjustable and may also include adjustable-height appendage-supporting members. Thus, the devices can accommodate patients of different heights and/or sizes. Additionally, the devices according to the present disclosure are collapsible such that the members making up the devices lie generally parallel, and in some cases alongside, one another. The devices are lightweight and easy to transport from patient to patient.

According to some examples of the present disclosure, a device for supporting a person's extremities includes a first pivotable arm and a second pivotable arm. An appendage-supporting member is coupled between the first and second pivotable arms. The device is collapsible such that the first and second pivotable arms lie generally parallel to one another. The device can be portable and free-standing or can be built into a platform such as a bed or a medical examination table.

Figure 1:
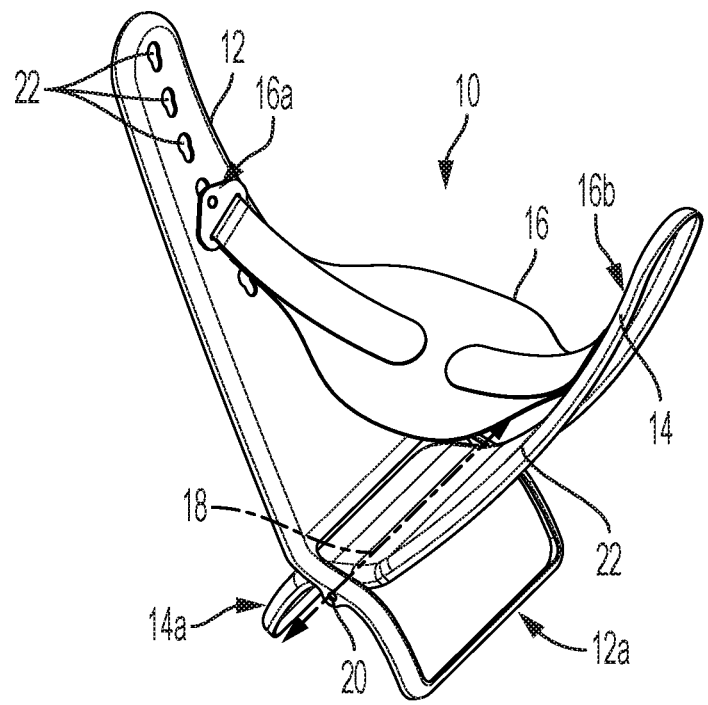
FIG. 1 illustrates a first example of a device for supporting a patient's extremities according to the present disclosure.

FIG. 1 illustrates a first example of a device 10 for supporting a patient's extremities according to the present disclosure. The device 10 includes a first pivotable arm 12 and a second pivotable arm 14. An appendage-supporting member 16 is coupled between the first and second pivotable arms 12, 14. Although the appendage-supporting member 16 is shown here in phantom, specific examples will be described herein below with respect to FIGS. 13-16. The first and second pivotable arms 12, 14 are pivotably connected to one another along a single pivot axis 18. In this example, a lower end 12a of first pivotable arm 12 is left open or with a cutout such that a lower end 14a of second pivotable arm 14 can pass therethrough. The pivotable arms 12, 14 are connected together by one or more pivot pins, such as shown at 20, along pivot axis 18. Pivoting about pivot axis 18 allows the device 10 to be collapsed such that the first and second pivotable arms 12, 14 lie generally parallel to one another. More specifically, when the device 10 is collapsed, the first and second pivotable arms 12, 14 lie alongside one another.

The appendage-supporting member 16 may be configured as a sling made of any type of material, including, but not limited to, fabric/cloth, plastic, elastomer, mesh/netting, foam, or any other material that is strong enough to support a patient's extremity, while still providing relative comfort to the patient. Opposite ends 16a, 16b of the appendage-supporting member 16 may be attached to the first and second pivotable arms 12, 14, respectively, by way of hooks, tabs, buttons, or other supporting devices attached thereto, which are then inserted into slots 22 provided in pivotable arms 12, 14. Note that slots 22 are provided at more or less equal heights along the height of pivotable arms 12, 14. Thus, appendage-supporting member 16 is able to be supported in a relatively horizontal manner between the first and second pivotable arms 12, 14. When the device 10 is assembled, with the appendage-supporting member 16 supported by slots 22 between first and second pivotable arms 12, 14, the patient's extremity is placed on the upper surface of appendage-supporting member 16, and rests there while the nurse or other medical personnel change the patient's dressing and/or clean his/her wound. Note that the slots 22 being provided at different heights along the pivotable arms 12, 14 allows the total height from a surface upon which the device 10 is supported to the upper surface of the appendage-supporting member 16 to be controlled, such that the patient's extremity can be elevated to different heights depending on need.

Figure 2:
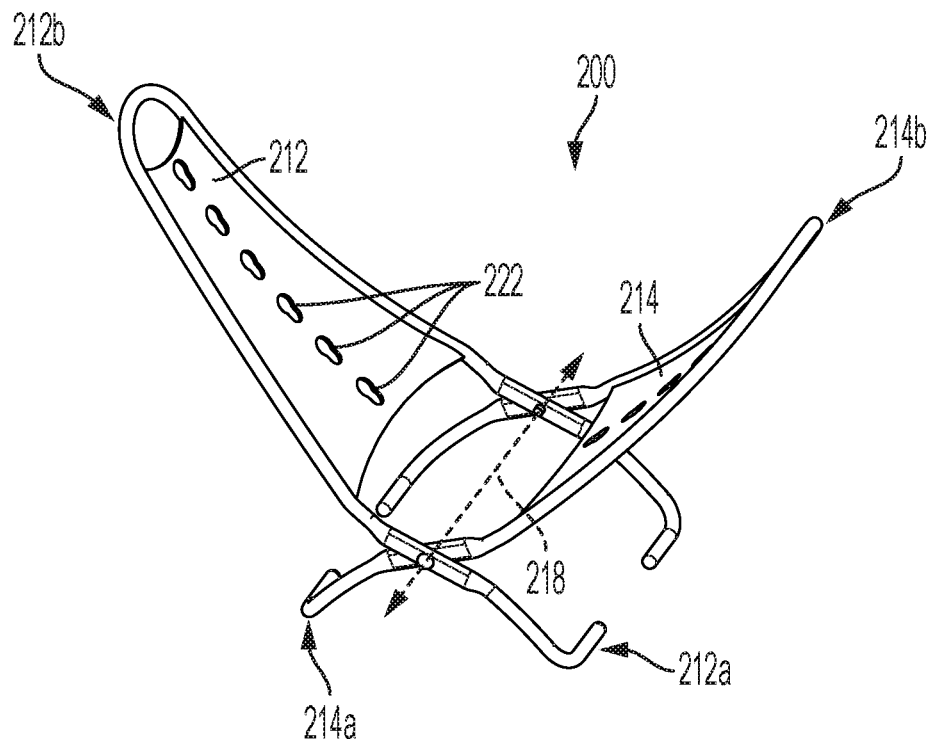
FIG. 2 illustrates a second example of a device according to the present disclosure.

FIG. 2 illustrates a second example of a device according to the present disclosure. The second example is similar to the first example shown in FIG. 1, with a few differences, as will be noted herein. Note that like features are denoted with the number "2" in front of them, such that the first pivotable arm is labeled 212, the second pivotable arm is labeled 214, etc. The device 200 shown herein differs from the first example of the device 10 in that the lower end 212a of first pivotable arm 212 does not have a bottom bar that extends across the full depth of the device 200. Additionally, the lower end 214a of second pivotable arm 214 is also open, and also does not have a bottom bar that extends the full depth of the device 200. Additionally, the upper ends 212b, 214b of first and second pivotable arms 212, 214, respectively, have cutouts or openings therein. These cutouts or openings serve as handles by which a person may carry the device 200 when it is in the collapsed position. Pivoting from the unfolded to the collapsed position is about pivot axis 218, and the pivotable arms 212, 214 may be coupled together by way of pivot pins 220a, 220b.

Although not shown herein, an appendage-supporting member similar to that shown at 16 in FIG. 1 can be provided and supported between the pivotable arms 212, 214 by way of slots 222.

Comparison of the first example with the second example bears noting that the first example, due to the presence of more structural material near its lower end, may have a lower center of gravity and may be better for supporting heavier extremities and/or heavier patients. Meanwhile, the cutouts at both first and second ends 212a, 214a and 212b, 214b of first and second pivotable arms 212, 214 in the second embodiment make the device 200 shown therein lighter and thus easier to carry. However, the first and second examples are similar to one another in that both provide first and second pivotable arms that are pivotably connected to one another along a single pivot axis, and when the devices are collapsed, the first and second pivotable arms lie alongside one another.

Figure 3:
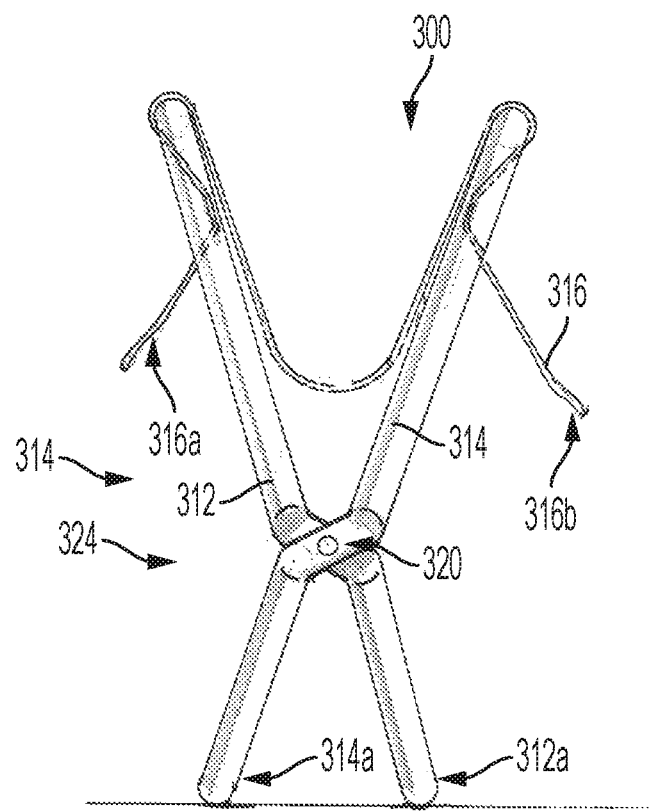
FIG. 3 illustrates a third example of a device according to the present disclosure.

A third example of a device 300, also in which the first and second pivotable arms 312, 314 are pivotably connected to one another along a single pivot axis 318, and when collapsed, lie alongside one another, is shown in FIG. 3. The pivotable arms 312, 314 are connected by pivot pins, one of which is shown at 320. A bushing 324 may be provided around the pivot pin 320 and between the pivotable arms 312, 314. Here, both lower ends 312a, 314a of pivotable arms 312, 314, respectively, may be left open, similar to the second example described hereinabove. However, in this example, the lower ends 312a, 314a have bars that do extend across the full depth of the device 300. Additionally, note that the appendage-supporting member 316 shown herein is configured differently and held to the pivotable arms 312, 314 differently than in the first and second examples. Further details of this appendage-supporting member 316 will be described herein below with respect to FIGS. 14-16.

Figure 4:
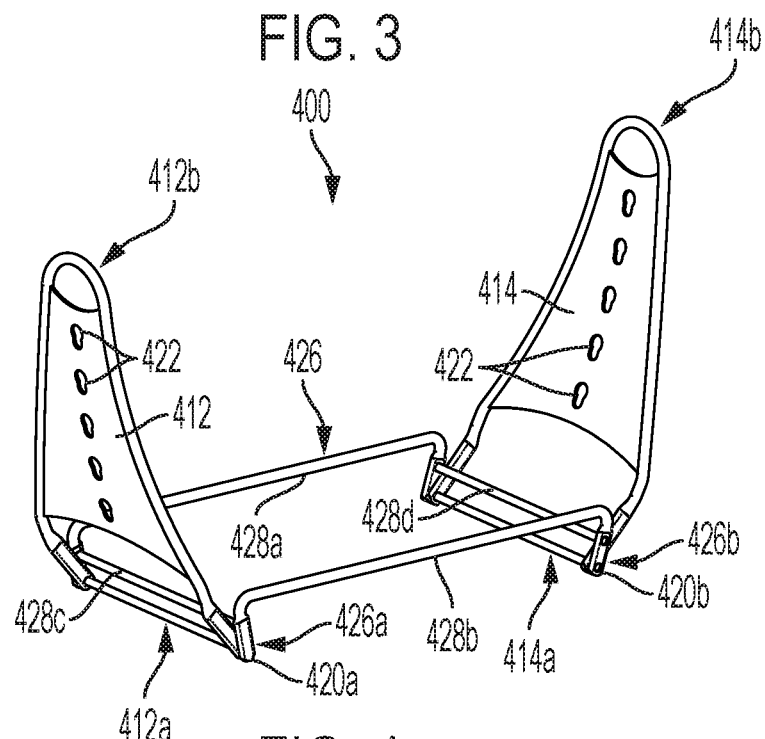
FIG. 4 illustrates a fourth example of a device according to the present disclosure.

A fourth example of a device according 400 to the present disclosure is shown in FIG. 4. Again, note that similar components are noted with a "4" in front of them, such that the first pivotable arm is labeled 412 and the second pivotable arm is labeled 414. Although not shown herein, an appendage-supporting member may be coupled between the first and second pivotable arms 412, 414, such as shown in FIG. 1, by way of insertion of portions of such appendage-supporting member into slots 422 on the pivotable arms 412, 414. The device 400 is collapsible such that the first and second pivotable arms 412, 414 lie generally parallel to one another, and more specifically lie alongside one another. However, in contrast to the first, second, and third examples, the device 400 shown herein further includes a base member 426, and the first and second pivotable arms 412, 414 are pivotable connected to opposite sides 426a, 426b of the base member 426. Specifically, the base member 426 is made up of four connected bars, including parallel bars 428a, 428b and parallel bars 428c, 428d connecting parallel bars 428a and 428b. Lower end 412a of first pivotable arm 412 is pivotably connected to parallel bars 428a, 428b by way of pivot pins, one of which is shown at 420a. Lower end 414a of second pivotable arm 414 is pivotably coupled to parallel bars 428a, 428b by way of pivot pins, one of which is shown at 420b. An appendage-supporting member, although not shown herein, can be connected between the pivotable arms 412, 414 by way of connection to slots 422.

The pivotable arms 412, 414 can be folded underneath the base member 426, where they lie generally parallel and alongside one another, in order to collapse the device 400. It should be understood that either the first pivotable arm 412 or the second pivotable arm 414 may be folded under the base member 426 first, followed by the other of the first pivotable arm 412 and the second pivotable arm 414.

Figure 5:
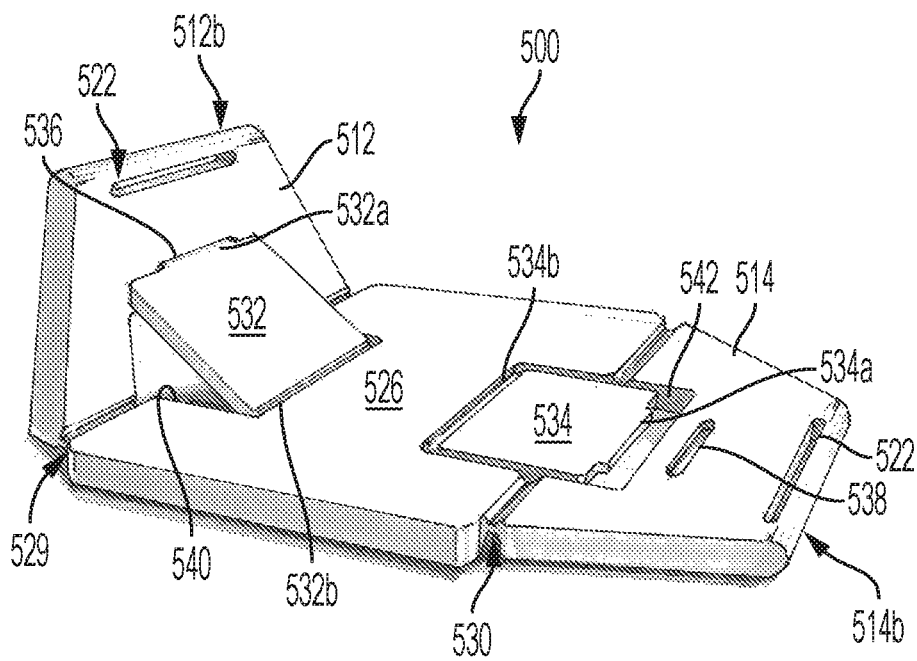
FIGS. 5 and 5A illustrate a fifth example of a device according to the present disclosure.
Figure 5A:
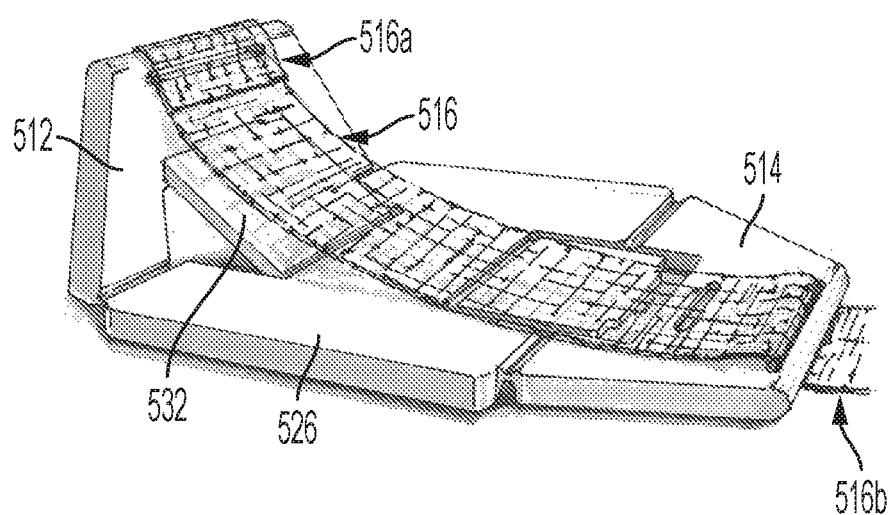

FIG. 5 illustrates another example of a device 500 according to the present disclosure, in which the first and second pivotable arms 512, 514 are also pivotably connected to opposite sides of a base member 526. The pivotable arms 512, 514 can be connected to the base member 526 by way of a pair of living hinges 529, 530. In an alternative example, pivot pins may be provided at these pivot locations. As shown, the first pivotable arm 512 may be rotated upwardly about living hinge 529 and held in an upright position by way of a support member 532, which has a protrusion 532a that fits into a slot 536 formed in first pivotable arm 512. A lower end of support member 532 is coupled by way of a living hinge 532b to the base member 526. Similarly, the second pivotable arm 514 can be rotated to an upright position about living hinge 530 and held in such position by way of pivoting of support member 534 about living hinge 534b and insertion of protrusion 534a within slot 538 in second pivotable arm 514. Note that the support members 532, 534, protrusions 532a, 534a, and slots 536, 538 could be configured other than that shown herein. Additionally, living hinges 532b, 534b could be replaced by other types of hinges, such as by pivot pins. Slots 522 are provided on each pivotable arm 512, 514, for receiving an appendage-supporting member (not shown). Although only one slot 522 is shown on each of the arms 512, 514, it should be understood that additional slots could be provided.

Note that although device 500 is not shown in a fully collapsed position, by removal of protrusion 532a from slot 536 in first pivotable arm 512, first pivotable arm 512 can be rotated downwardly, such that it lies parallel to base member 526 and second pivotable arm 514. In the fully collapsed position, support members 532 and 534 lie fit within recesses 540, 542, which provides the device 500 with a completely flat profile when collapsed.

Figure 6:
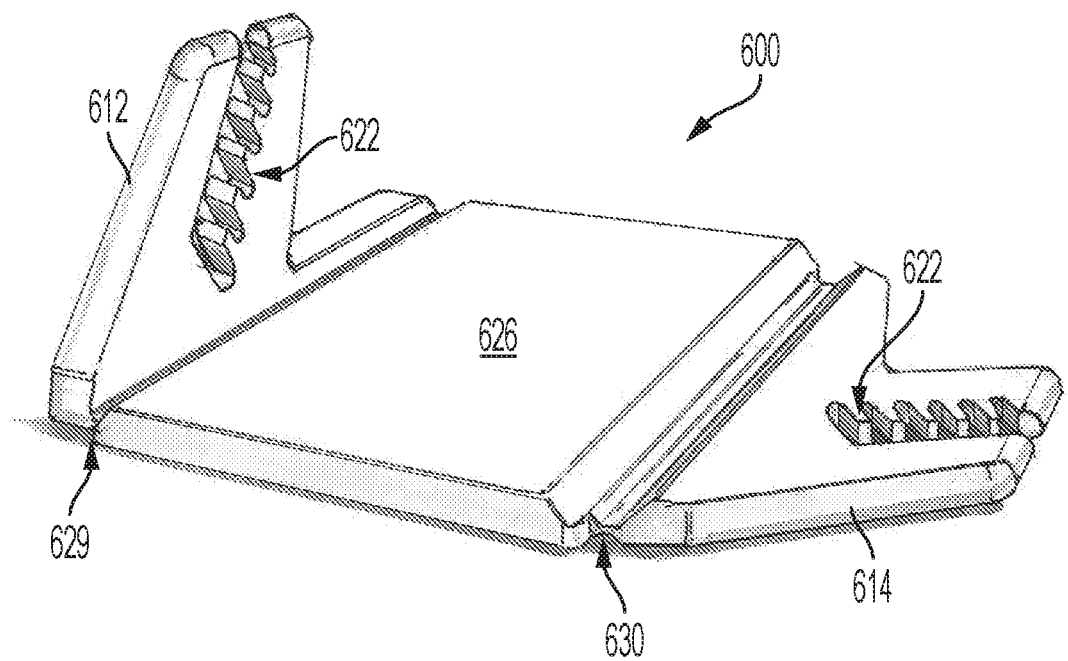
FIG. 6 illustrates a sixth example of a device according to the present disclosure.

FIG. 6 shows a sixth example of a device 600 according to the present disclosure. Similar to the fifth example, the sixth example includes first and second pivotable arms 612, 614, both of which are connected to a base member 626 at opposite sides of the base member 626 by way of living hinges 629, 630. Although the device 600 shown herein is not shown in a fully collapsed position, it should be understood that first pivotable arm 612 can be rotated downwardly about living hinge 629 such that it lies parallel to base member 626 and second pivotable arm 614. Vertically indexed slots 622, here arranged in a toothed pattern, are provided for allowing for vertical adjustment of appendage-supporting member (not shown) such as a molded roller or bolster, made of a material such as plastic or foam. However, other types of appendage-supporting members could be provided, so long as those members had protrusions on either end capable of interacting with slots 622 in first and second pivotable arms 612, 614.

Figure 7:
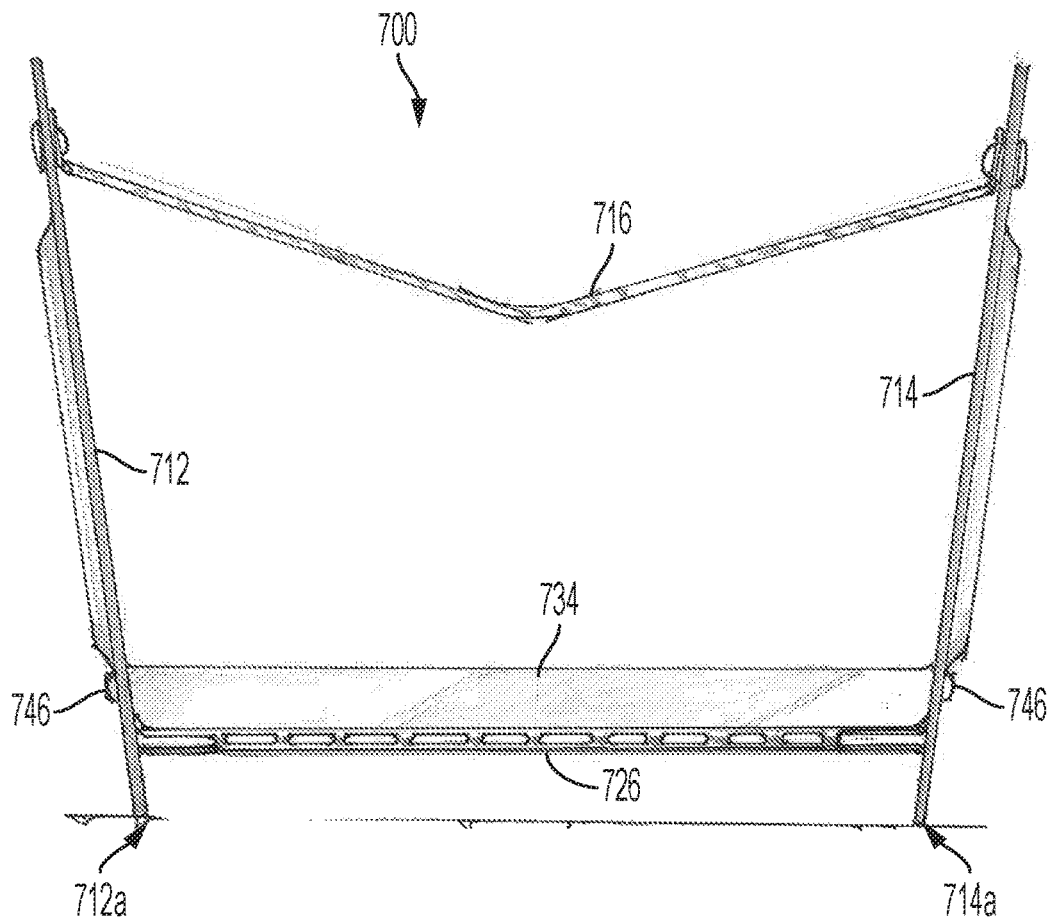
FIGS. 7 and 7A illustrate a seventh example of a device according to the present disclosure.
Figure 7A:
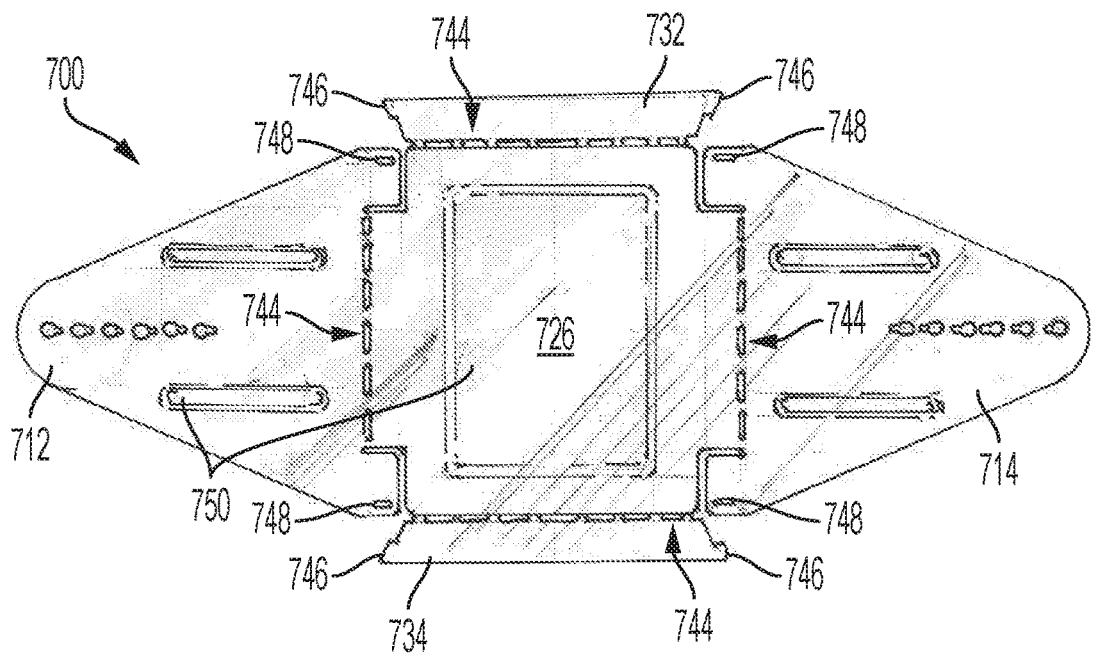

FIGS. 7 and 7A show a seventh embodiment of a device 700, which device 700 includes first and second pivotable arms 712, 714 and appendage supporting-member 716 coupled between the first and second pivotable arms 712, 714. Similar to the fifth and sixth embodiments, the seventh embodiment also includes a base member 726 to which the first and second pivotable arms 712, 714 are pivotably connected. As shown in FIG. 7A, the device 700 may be made of metal, plastic, or another relatively rigid material, with perforations such as those shown at 744. The device 700 may also be provided with stamped recesses, such as shown at 750, to provide rigidity to the base member 726 and first and second pivotable arms 712, 714.

FIG. 7A shows the device 700 in a fully collapsed position in which the first and second pivotable arms 712, 714 are parallel to one another and parallel to the base member 726. The pivotable arms 712, 714 and support members 732, 734 may be pivoted upwardly about the perforations 744. Thereafter, locking tabs 746 shown on each of the support members 732, 734 may inserted into locking slots 748 at lower ends of first and second pivotable arms 712, 714. Such insertions of tabs 746 into slots 748 holds the first and second pivotable arms 712, 714 in an upright position, after which the appendage-supporting member 716 may be inserted into slots 722 as will be described further herein below. FIG. 7 shows the device 700 in an assembled position, in which the locking tabs 746 have been inserted through the locking slots 748. Note that the lower ends 712a, 714a of first and second pivotable arms are in contact with the surface upon which the device 700 sits.

Figure 8:
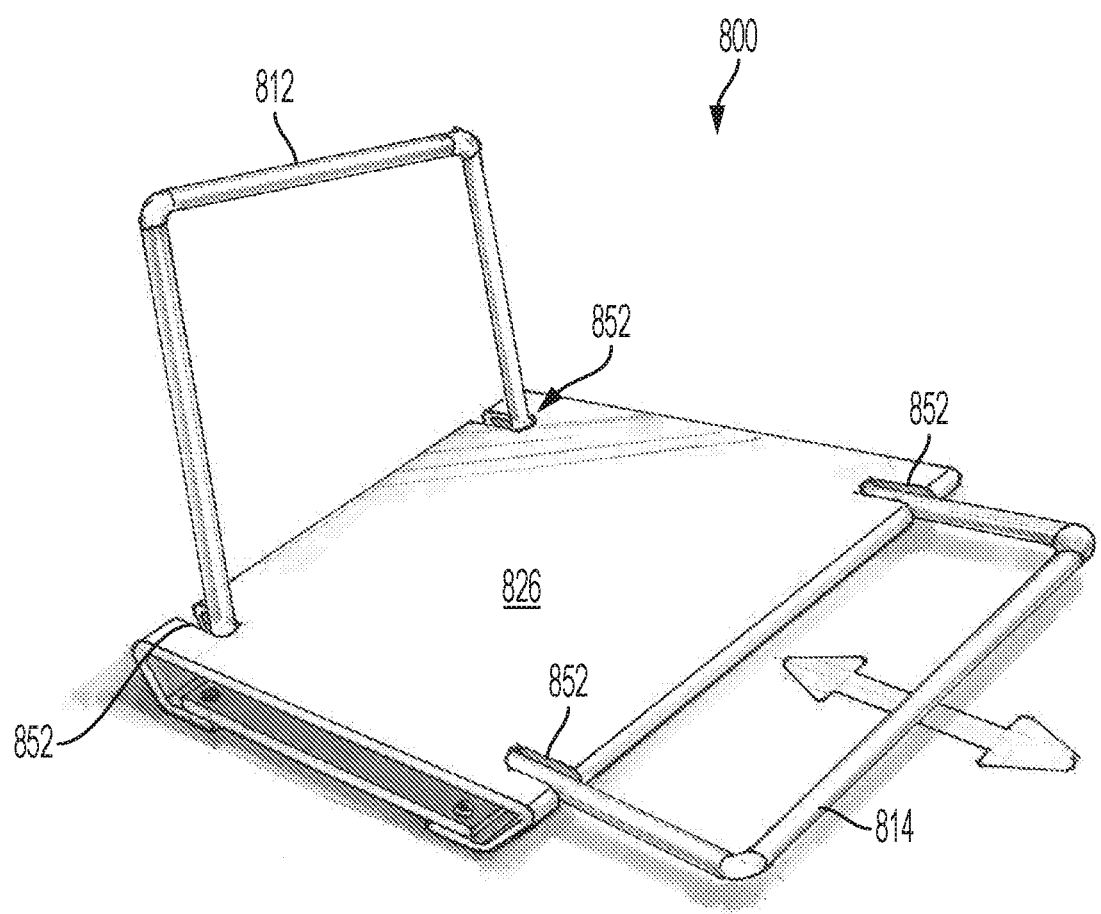
FIG. 8 illustrates an eighth example of a device according to the present disclosure.

FIG. 8 shows an eighth embodiment of a device 800 according to the present disclosure. Here, the device 800 includes first and second pivotable arms 812, 814 connected to opposite sides of a base member 826. The base member 826 may be made of one or several sheets of rigid material bent into a shape having an open cross section, such as a trapezoid (shown), although other configurations such as a rectangle would suffice. The open cross section of the base member 826 allows the first and second pivotable arms 812, 814 to be pivoted outwardly from the base member 826 and then slid within the base member 826 as shown by the arrows. Thus, the first and second pivotable arms 812, 814 can be stored within the base member 826 in a configuration in which the arms 812, 814 lie generally parallel to and alongside one another. Such insertion of the first and second pivotable arms 812, 814 within the base member 826 is accomplished by way of sliding lower ends 812a, 814a of the pivotable arms 812, 814, respectively into slots 852 provided within base member 826. Although not shown herein, an appendage-supporting member could be coupled between the first and second pivotable arms 812, 814.

Figure 9:
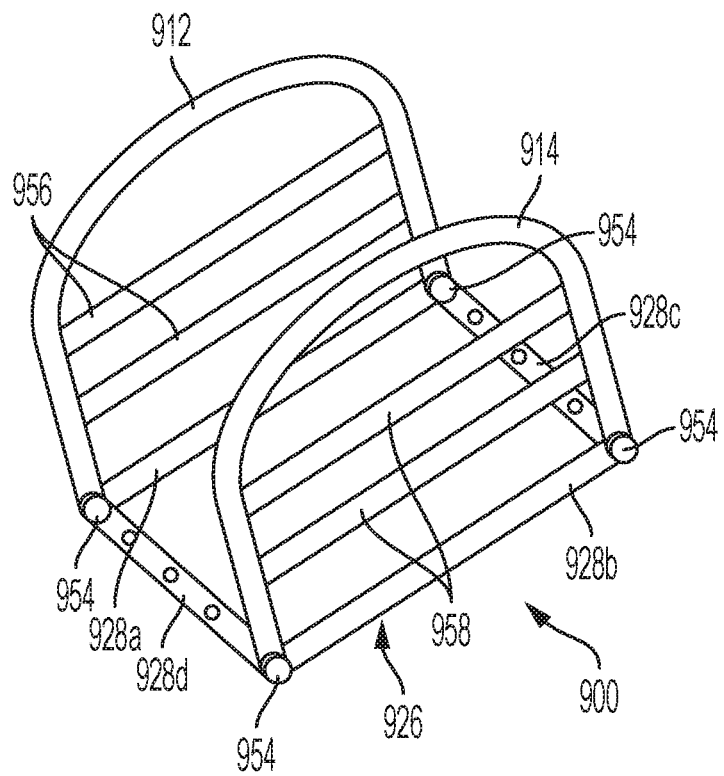
FIG. 9 illustrates a ninth example of a device according to the present disclosure.
Figure 10A:
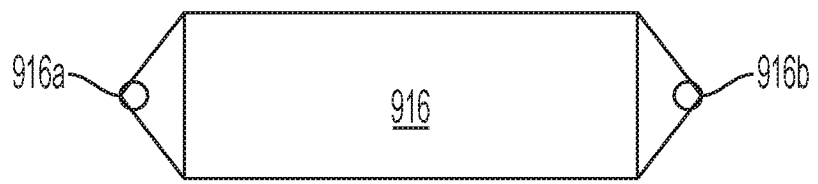
FIGS. 10A and 10B illustrate an appendage support for use with the device of FIG. 9.
Figure 10B:
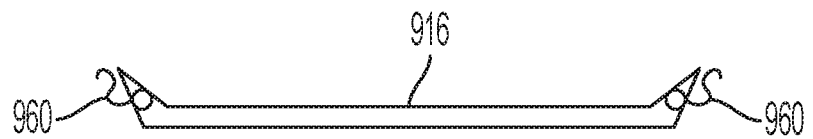

A ninth embodiment of a device 900 according to the present disclosure is shown in FIGS. 9 and 10A-B. In this embodiment, the device 900 includes first and second pivotable arms 912, 914. First and second pivotable arms 912, 914 are connected to opposite sides of a base member 926, including four connected bars 928a-928d. The bars 928c, 928d can be telescoping tubes, and may be adjusted in length (to adjust the total width of the device 900) by way of spring-loaded buttons in holes. Each of the bars 928a-928d may be hinged to the first and second pivotable arms 912, 914 by way of hinges 954. The hinges 954 allow the first and second pivotable arms 912, 914 to be folded inwardly on top of the base member 926, below the base member 926, or outwardly to lie parallel to and on either side of the base member 926.

Parallel bars 956, 958 extend in the depth direction of the first and second pivotable arms 912, 914. These bars 956, 958 allow for an appendage-supporting member 916 (FIGS. 10A-B) to be suspended between the first and second pivotable arms 912, 914. In this embodiment, the appendage-supporting member 916 may be provided with reinforced holes 916a, 916b at either end, through which S-hooks 960 may be inserted. Opposite ends of the S-hooks 960 may be connected to the bars 956, 958.

Figure 11:
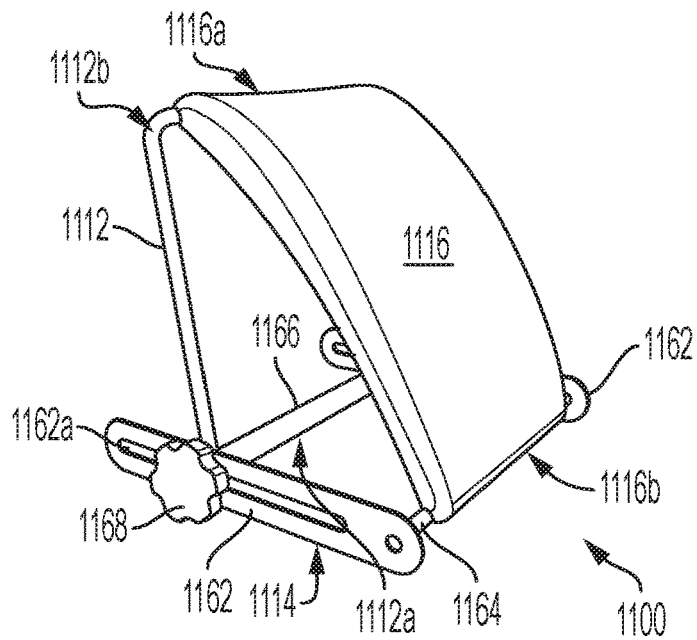
FIGS. 11-11B illustrate a tenth example of a device according to the present disclosure.
Figure 11A:
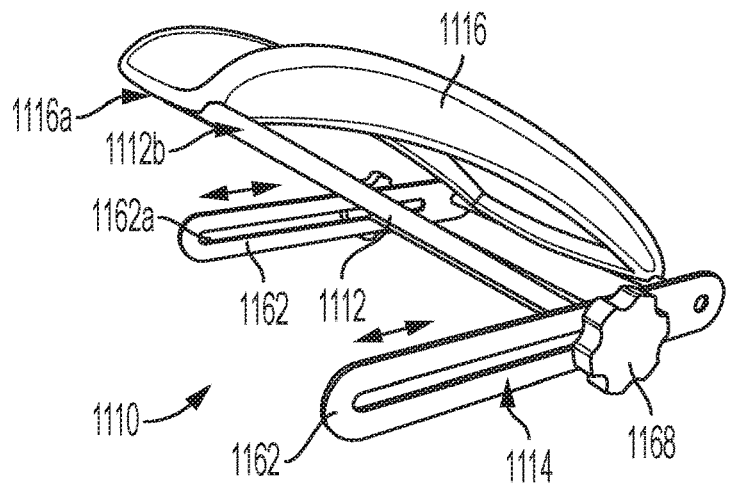
Figure 11B:
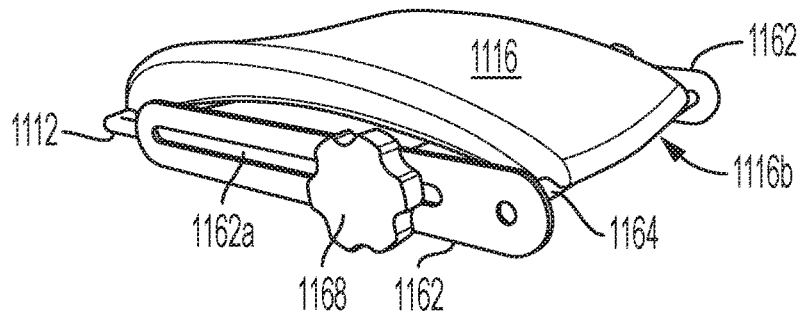

Yet another example of a device 1100 according to the present disclosure is shown in FIGS. 11-11B. The device 1100 includes a first pivotable arm 1112 and a second pivotable arm 1114. In fact, the second pivotable arm 1114 may be comprised of three connected members, including parallel arms 1162 connected by way of connecting member (bar) 1164. An appendage-supporting member 1116 is coupled between the first and second pivotable arms 1112, 1114. More specifically, a first end 1116a of appendage-supporting member 1116 is coupled to end 1112b of first pivotable arm 1112, and opposite end 1116b of appendage-supporting member 1116 is coupled to bar 1164 of second pivotable arm 1114. The appendage supporting member can be a molded member made of plastic, metal, foam, or elastomer.

A reinforcing bar 1166 serves as end 1112a of first pivotable arm 1112. Opposite ends of the reinforcing bar 1166 extend through slots 1162a in arms 1162. Knobs 1168 are provided at either end of reinforcing bar 1166 for tightening or loosening reinforcing bar 1166 with respect to slots 1162a. When loosened, the reinforcing bar 1166 can be slid in the direction of the arrows shown in FIG. 11A in order to raise or lower the height of appendage-supporting member 1116 with respect to a surface upon which the device 1100 is resting. Once a desired height/angle is achieved, the knobs 1168 may be tightened on both sides of the device 1100 to fix the first arm 1112 and appendage-supporting member 1116 with respect to the second arm 1114, i.e., with respect to the arms 1162.

The device 1100 is shown in a nearly fully extended position in FIG. 11 and in a fully collapsed position in FIG. 11B. It can be seen that because the first pivotable arm 1112 is slidably connected to the second pivotable arm 1114, the device 1100 is able to be collapsed such that the first and second pivotable arms 1112, 1114 lie generally parallel to and alongside one another.

Figure 12:
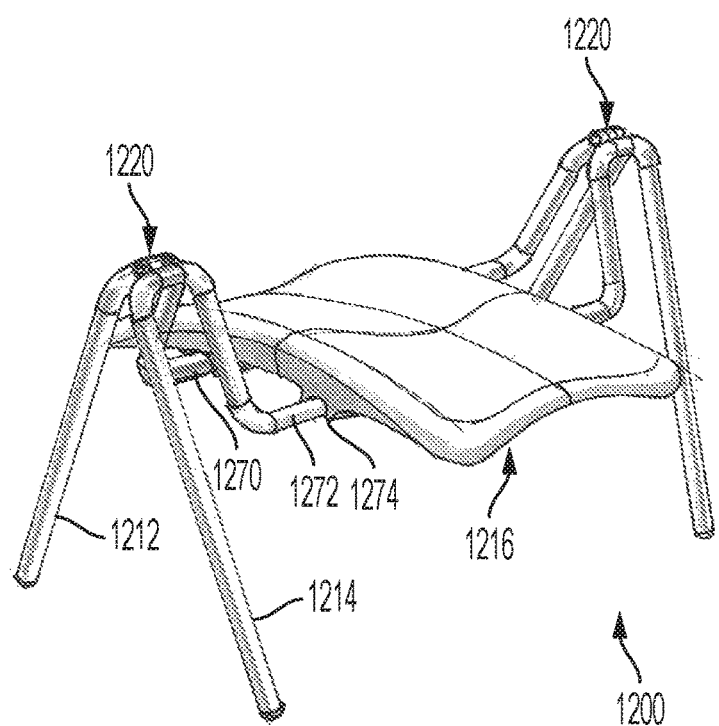
FIGS. 12 and 12A illustrate an eleventh example of a device according to the present disclosure.
Figure 12A:
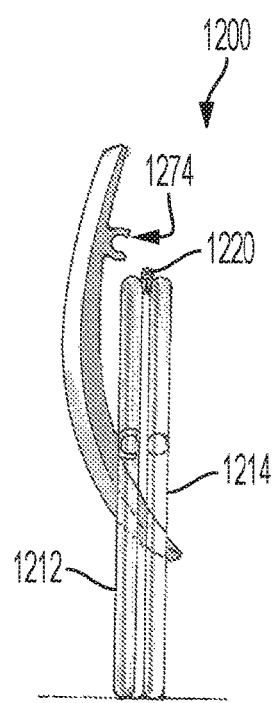

FIGS. 12 and 12A show a twelfth example of a device 1200 according to the present disclosure. First and second pivotable arms 1212, 1214 are connected along a pivot axis, such as by pivot pins or hinges 1220. Instead of having separate bars or cross members extending between the sides of pivotable arms 1212, 1214, each arm 1212, 1214 has a bar 1270, 1272 depending therefrom. The appendage-supporting member 1216 is supported on the bars 1270, 1272 by way of C-shaped moldings on the underside of the appendage-supporting member 1216, as shown at 1274. The C-shaped moldings 1274 can be clipped to the bars 1270, 1272. When the device is to be collapsed, as shown at FIG. 12A, the C-shaped moldings 1274 may be unsnapped from the bar 1272 and/or from the bar 1270. Thus, the first and second pivotable arms 1212, 1214 can be pivoted about hinges 1220 and collapsed such that they lie generally parallel to and alongside one another.

FIGS. 13-16 are now referred to in order to describe several examples of appendage-supporting members and how the appendage-supporting members may be coupled between the first and second pivotable arms.

Figure 13:
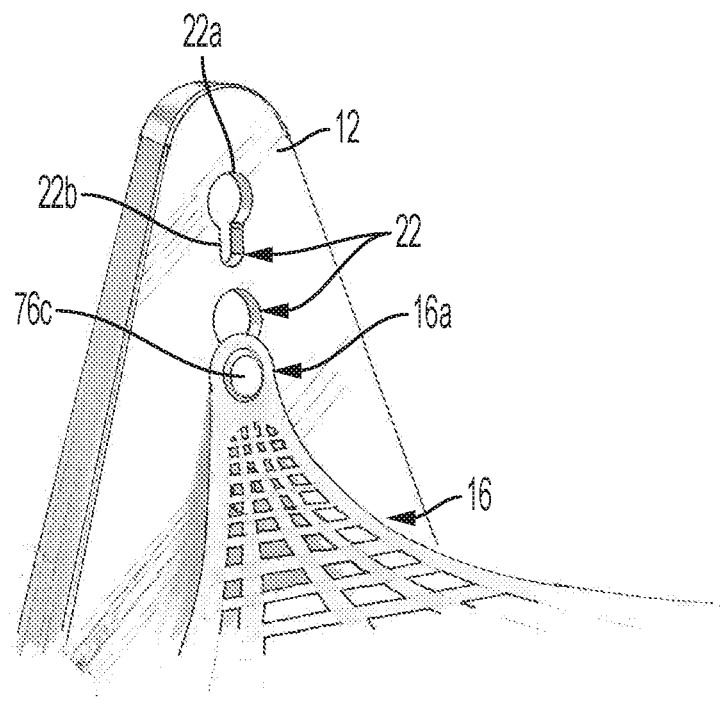
FIGS. 13-13B illustrate details of one example of an appendage support for some devices according to the present disclosure.
Figures 13A, 13B:
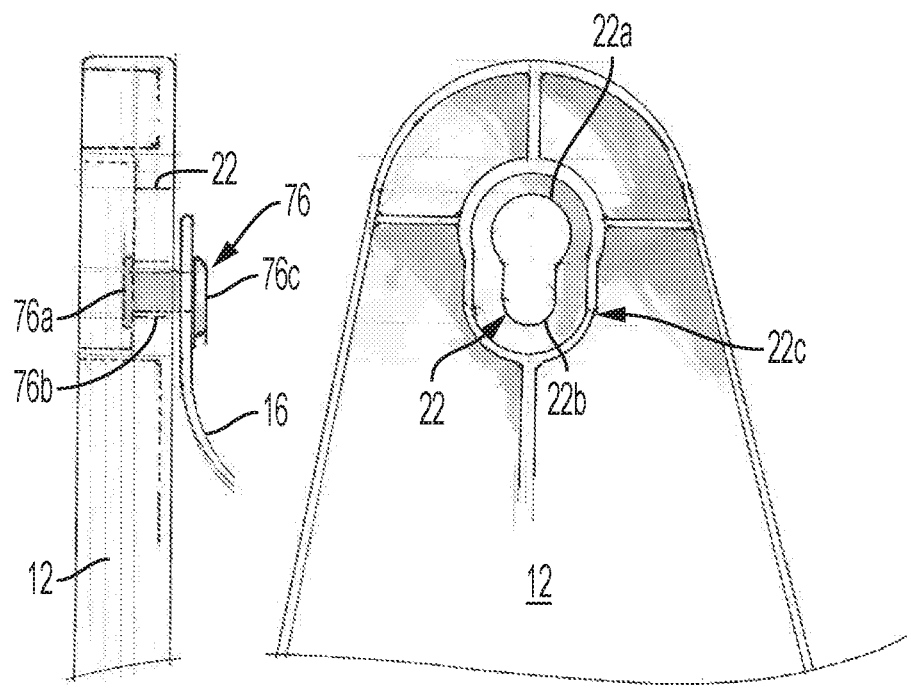

FIGS. 13-13B illustrate an example of how an appendage-supporting member 16 may be coupled to a first pivotable arm in a device such as that shown in FIG. 1, 2, 4, or 7. Note that for simplicity, the example of FIGS. 13-13B will be described only with respect to the first embodiment of the device 10. As shown in FIGS. 13 and 13A, the end 16a of appendage-supporting member 16 can be provided with a tab or button 76. A flange 76c at one of the tab or button 76 holds end 16a of appendage-supporting member 16, while an opposite flange 76a on tab or button 76 can be inserted through slot 22 in first pivotable arm 12. As shown in FIG. 13A, the flange 76a that fits through slot 22 need not extend through the full depth of pivotable arm 12, but could instead by configured to be recessed therein. The slot 22 is provided with the shape of a key-hole, and has a larger circular area 22a and a lower slotted area 22b. As is known to those having ordinary skill in the art, the flange 76a provided at end of tab or button 76 can be inserted through the larger circular area 22a, and then the barrel shaped portion 76b of tab or button 76 can be slid down into receiving slot 22b in order to hold the tab or button 76 within slot 22. FIG. 13B shows how slot 22 may be provided as an injection molded slot, with a surrounding reinforcement area 22c that provides strength to the slot 22.

Figure 14:
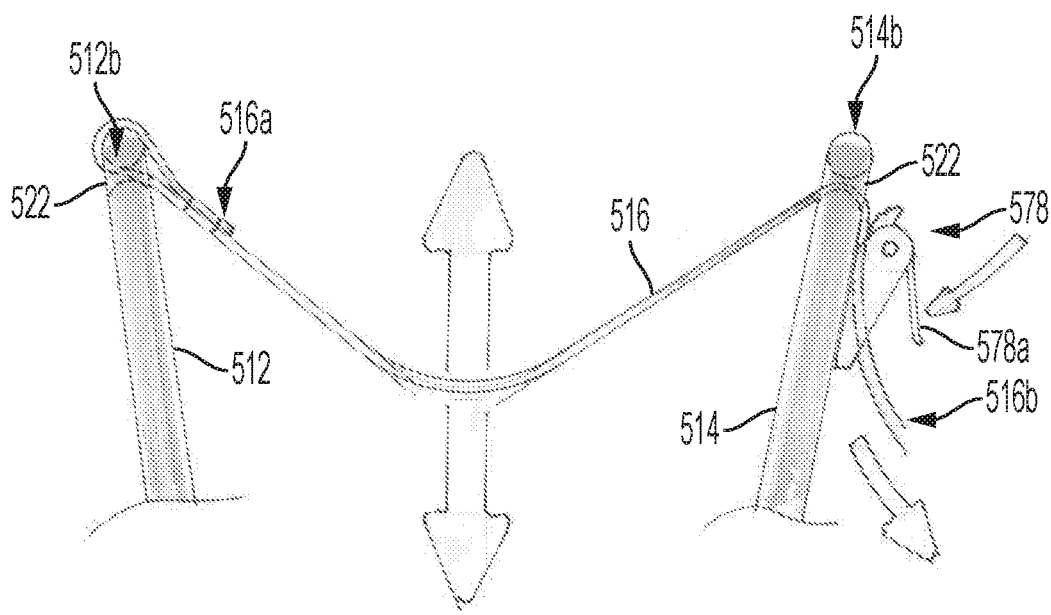
FIGS. 14 and 14A illustrate another example of an appendage support according to the present disclosure.
Figure 14A:
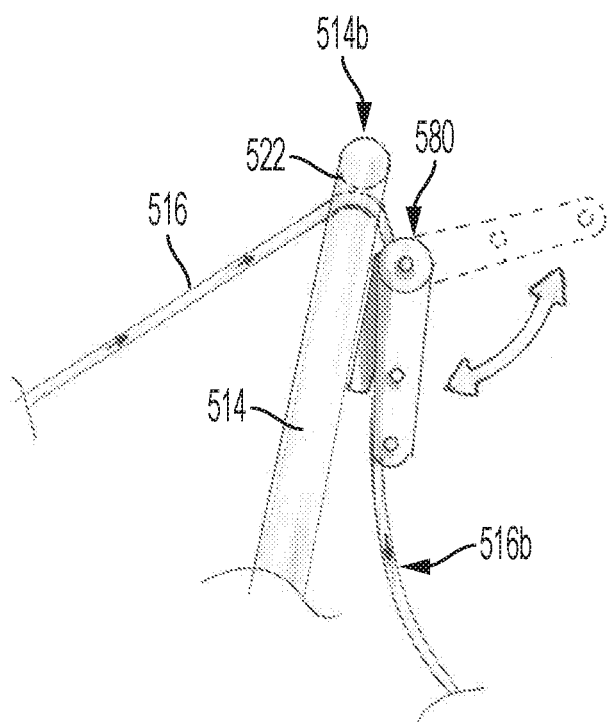

The appendage-supporting member of FIGS. 14 and 14A can be used with the embodiments of the device shown in FIG. 3, 5, 8, or 9. However, for exemplary purposes, the appendage-supporting member 516 will be referred to with respect to the device 500 of FIG. 5. The first end 516a can be looped through slot 522 at end 512b of pivotable arm 512. First end 516a can then be secured to appendage-supporting member 516 by way of sewing, glue, or other fastening mechanisms known to those having ordinary skill in the art. Opposite end 516b can be slid through slot 522 in end 514b of pivotable arm 514. End 516b can then be routed through a ratcheting device 578, having a handle 578a that can be moved in the direction of the arrow shown in FIG. 14 to tighten the appendage-supporting member 516 within the ratcheting device 578. When the ratcheting device 578 is loosened, the appendage-supporting member 516 can be pulled further through the slot 522 and ratcheting device 578 in the direction of the arrow as shown to raise the height of the appendage-supporting member 516, or can be played out in an opposite direction, in order to lower the appendage-supporting member 516. FIG. 14A shows a similar adjustment mechanism employing a clamping device 580, which may be moved between the positions shown in solid lines and in phantom in order to loosen or secure the material of the appendage-supporting member 516 with respect to the second pivotable arm 514.

Figure 15:
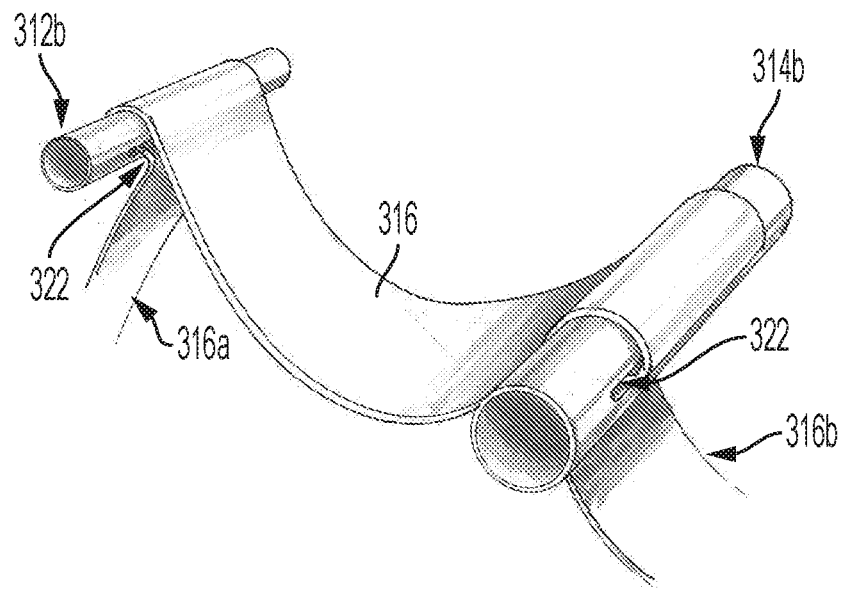
FIG. 15 illustrates another example of an appendage support according to the present disclosure.

FIG. 15 shows an embodiment of an appendage-supporting device that can be used with the device shown hereinabove in FIG. 3, 8, or 9. The appendage-supporting member 316 will be described, however, with respect to the device 300 of FIG. 3 for the purposes of simplicity. Here, the bars provided at ends 312b, 314b of pivotable arms 312, 314, respectively, are shown in isolation. Each of these bars may be provided with a slot 322 through which the ends 316a and 316b of appendage-supporting member 316 are threaded. The ends 316a, 316b could then connected to the underside of appendage-supporting member 316, or left to hang loose, depending on the size of the slots 322 and the surface coefficient of friction of the material used to manufacture the device.

Figure 16:
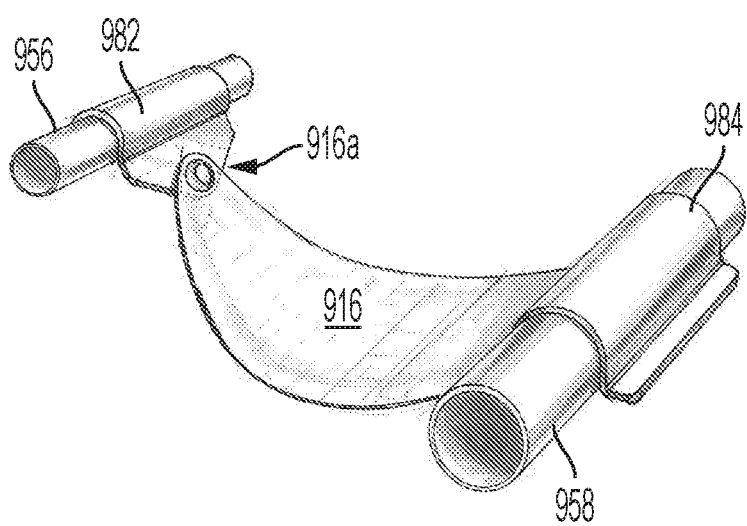
FIG. 16 illustrates another example of an appendage support according to the present disclosure.

FIG. 16 show another embodiment of an appendage-supporting device that could be used with several of the devices noted hereinabove. Specifically, this example will be described with respect to the device 900 of FIG. 9. However, it should be noted that several bars at different heights are shown in the embodiments of FIGS. 3 and 8 as well, with which the assembly of FIG. 16 could be used. Here, appendage-supporting member 916 can be connected at end 916a to a clip 982, which may be a molded or extruded member that fits around the bar 956. Such connection between end 916a and clip 982 may be provided by way of a button, snap, pivot pin, rivet, or other known device. A clip 984 may be provided for connection to bar 958. This clip 984 is connected to end 916b of appendage-supporting member 916 by way of a similar pivot pin, snap, rivet, etc. The clip 984 is able to be moved from one bar 958 to another in order to adjust the height of the appendage-supporting member 916 on the device 900. Note that both ends of the device 900 could be adjustable in such a manner.

Figure 17:
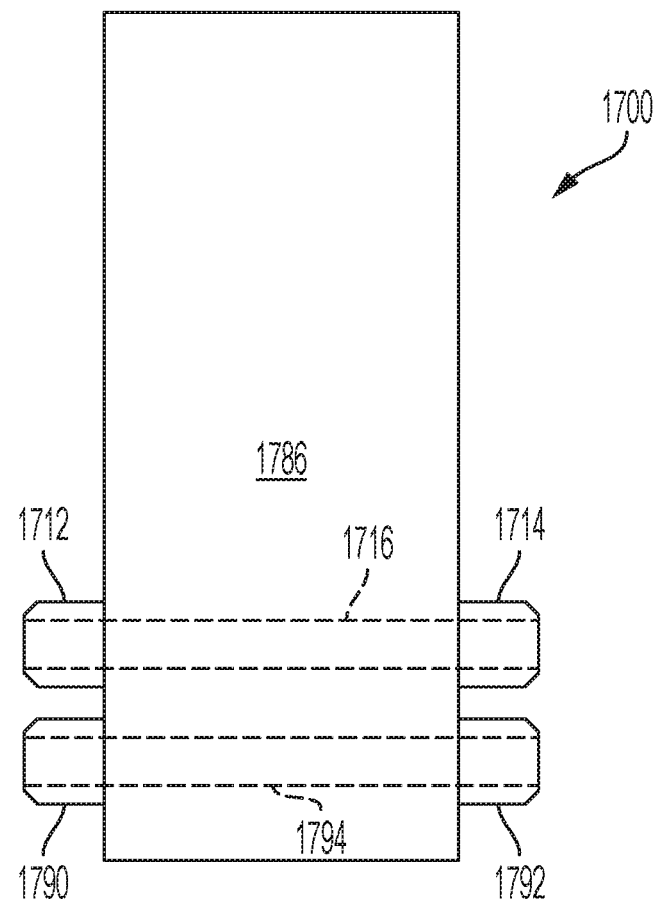
FIGS. 17-17C illustrate an embodiment of a device for supporting a patient's extremities that is built into a platform.
Figure 17A:
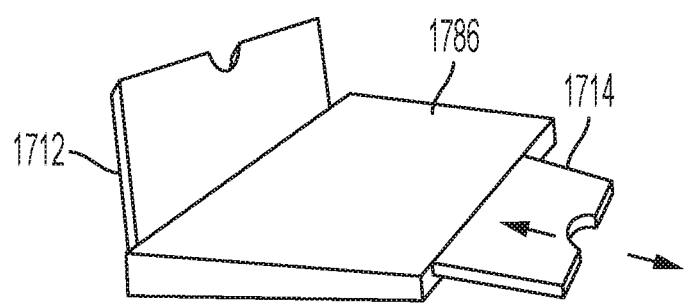
Figure 17B:
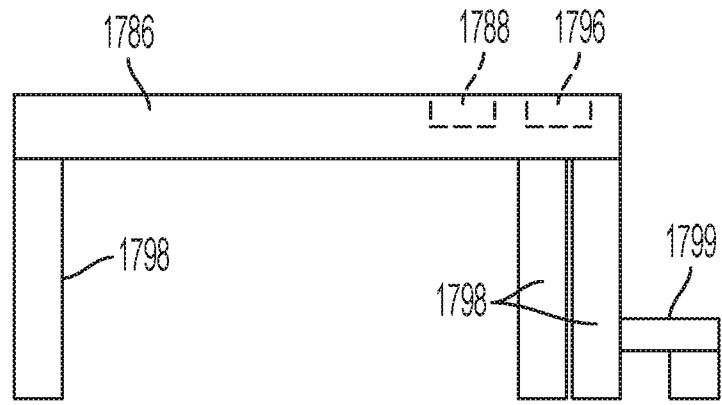
Figure 17C:
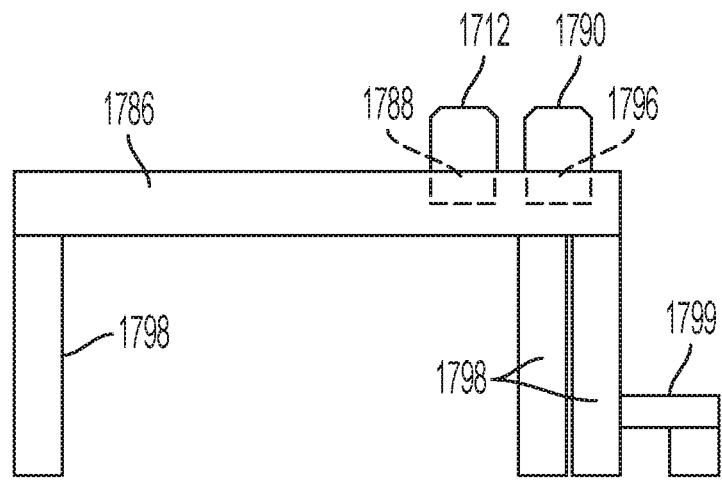

FIGS. 17-17C show another embodiment of a device for supporting a patient's extremities. The device includes a first pivotable arm 1712, a second pivotable arm 1714, and an appendage-supporting member 1716 (shown in phantom) coupled between the first and second pivotable arms 1712, 1714. Here, the device 1700 further includes a platform 1786, such as a bed or table, for supporting the patient's body. The first and second pivotable arms 1712, 1714 are retractable within the platform 1786, as is shown by the arrows in FIG. 17A. More specifically, each arm 1712 or 1714 can be pivoted about a pivot provided within the platform 1786 and slid into a slot 1788 (see FIG. 17B) provided within the top or on each side of platform 1786. Additional pivotable arms 1790, 1792 may be provided with an additional appendage-supporting device 1794 coupled therebetween. These arms 1790, 1792 may be retractable within slots or recesses 1796 provided in the sides or the top of the platform 1786.

The platform 1786, if designed as a bed or patient table, may include legs 1798 and a retractable stool 1799, as is known to those having ordinary skill in the art. Note that any or all of the arms 1712, 1714, 1790, 1792 may be pivotable and/or retractable by way of manual actuation by a user, or by way of mechanical actuation in response to simple pressing of a button. In the latter instance, motors or other mechanized devices may be provided. The operator may choose whether one set of arms 1712, 1714 or both sets of arms, including 1790, 1792, are to be positioned in an upright fashion with respect to the platform 1786 as shown in FIG. 17C. This would depend on the patient's and care provider's need. Once the desired arms have been elevated with respect to the platform 1786, the appendage-supporting member 1716 and/or 1794 could then be manually attached by the care provider between the arms 1712, 1714 or 1790, 1792, respectively.

Figure 18:
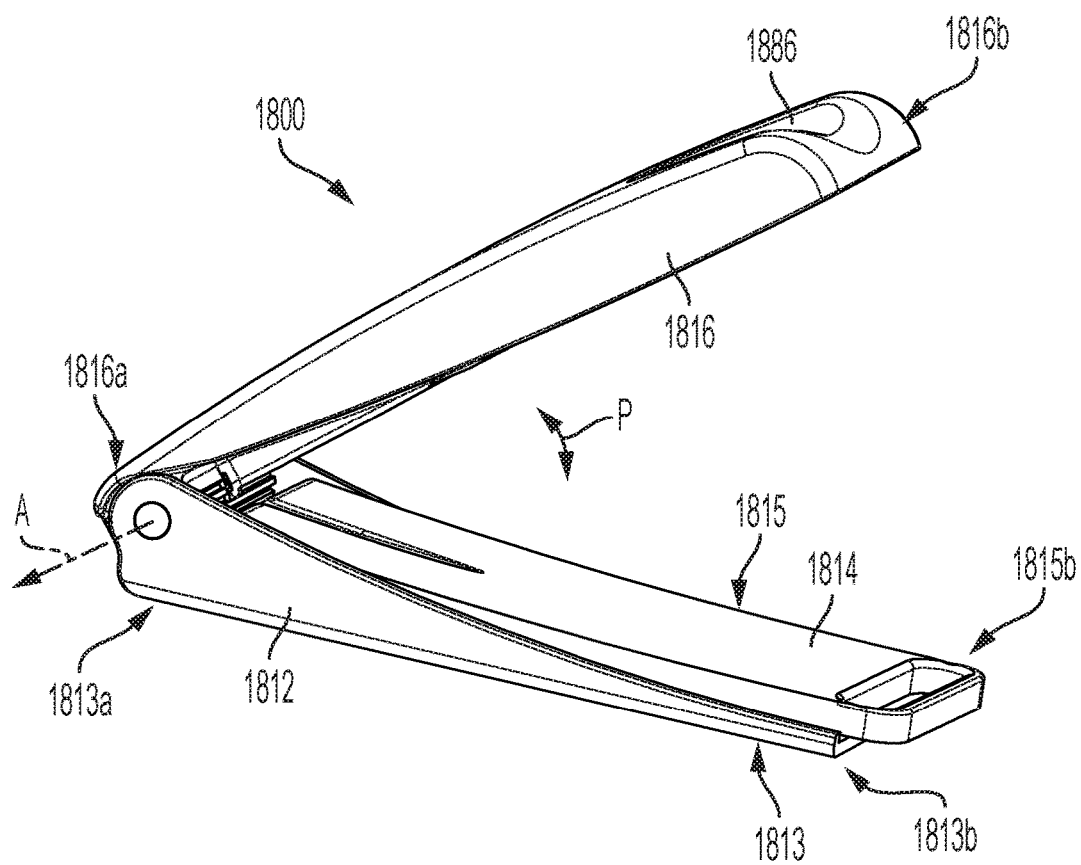
FIGS. 18-19 illustrate yet another example of a device for supporting a person's extremities according to the present disclosure.

FIGS. 18-29 illustrate yet another embodiment of a device according to the present disclosure. The device 1800 for supporting a person's extremities comprises a first arm 1812 and a second arm 1814 pivotably coupled to the first arm 1812. An appendage support 1816 is coupled to the first and second arms 1812, 1814. The device 1800 is configurable in a use position, one example of which is shown in FIG. 18, in which the appendage support 1816 is not parallel to at least one of the first and second arms 1812, 1814 while remaining coupled to the first and second arms 1812, 1814. When the device 1800 is in the use position, the first arm 1812 serves as a base 1813 that is configured to rest on a generally horizontal surface (not shown, but as can readily be envisioned by one having ordinary skill in the art), and the appendage support 1816 is configured to extend upwardly away from the generally horizontal support surface. The upwardly angled appendage support 1816 can thereby elevate the person's extremity (e.g., limb) above the horizontal support surface for treatment. To that end, the appendage support 1816 includes a depression 1886 for positioning the person's extremity thereupon.

Figure 19:
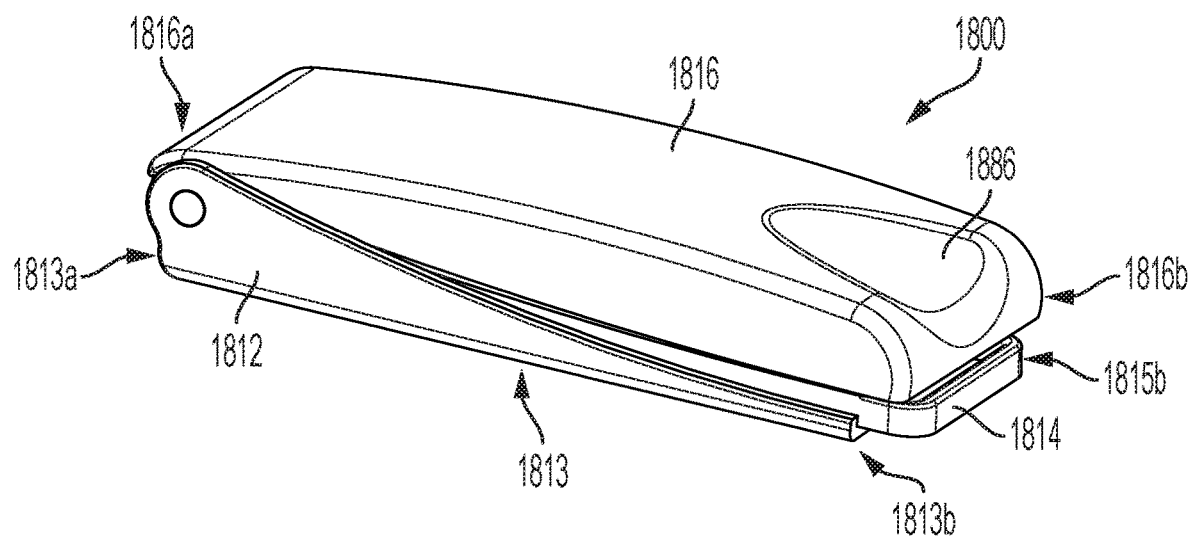

The device 1800 is also configurable in a collapsed position, shown in FIG. 19, in which the first and second arms 1812, 1814 and the appendage support 1816 are generally parallel to one another while remaining coupled to one another. As shown, when the device 1800 is in the collapsed position, the appendage support 1816 lies immediately alongside at least one of the first and second arms 1812, 1814. Here, the appendage support 1816 lies immediately alongside the second arm 1814, and the second arm 1814 lies immediately alongside the first arm 1812. The collapsed position facilitates transport and storage of the device 1800 when not in use.

Figure 20:
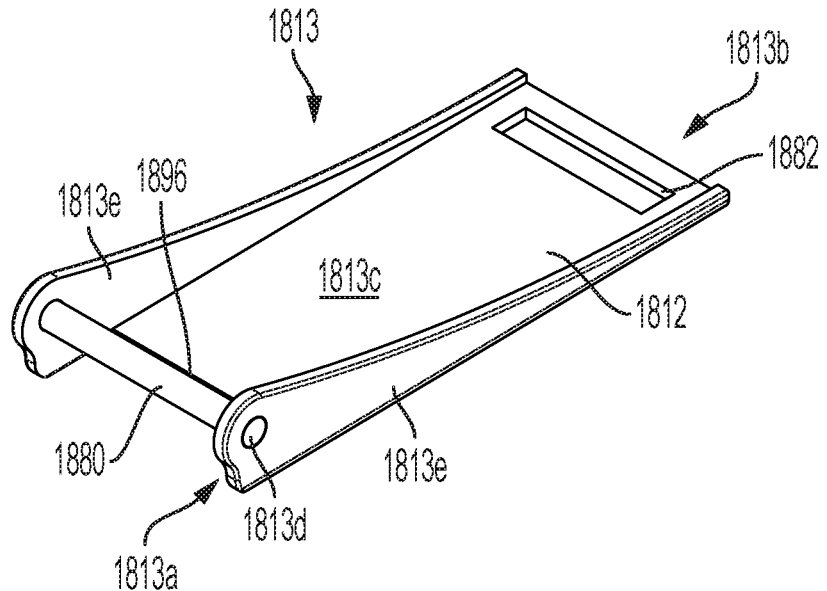
FIGS. 20 and 21 illustrate a base of the device of FIGS. 18 and 19.
Figure 21:
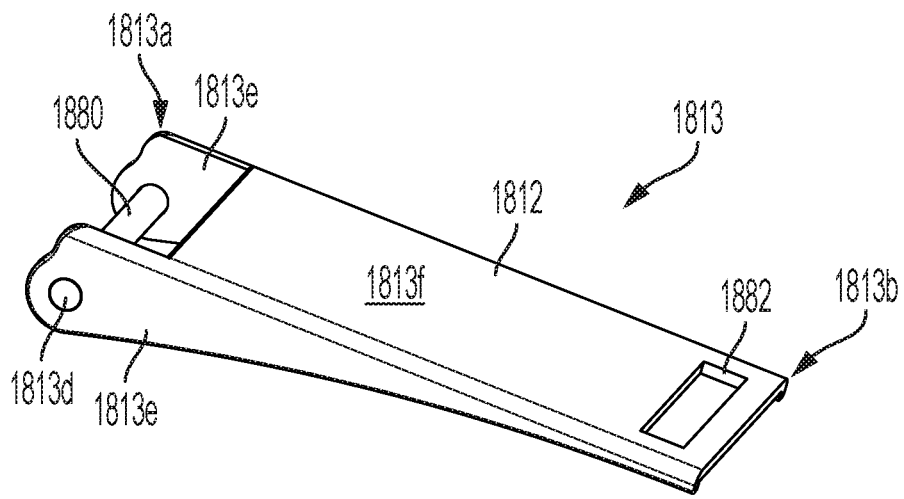

Referring now to FIGS. 20 and 21, the device 1800 comprises an elongated base 1813 having a first end 1813*a* and a second end 1813*b*. A pivot rod 1880 is coupled to the first arm 1812, more specifically at the first end 1813*a* of the base 1813, such as by insertion of the pivot rod 1880 through receiving holes 1813*d* in upwardly projecting sidewalls 1813*e* extending longitudinally along opposite sides of the first arm 1812. The sidewalls 1813*e* are shown as having a sloped configuration, with a higher height near the first end 1813*a* of the base 1813 and a lower height near the second end 1813*b* of the base 1813; however, the height and/or geometry of the sidewalls 1813 could be different than shown. The sidewalls 1813*e* extend further longitudinally than does the first arm 1812, such that the base 1813 comprises an edge acting as a fulcrum 1896, the purpose of which will be described further herein below. In general, the sidewalls 1813*e* and receiving holes 1813*d* therein should project above the top surface 1813*c* of the base 1813 (i.e., above the first arm 1812) in order to allow for placement and coupling of the second arm 1814 and appendage support 1816, as will also be described herein below. The base 1813 also comprises a recess 1882 near the second end 1813*b* thereof. As shown, the recess 1882 extends through the top surface 1813*c* and bottom surface 1813*f* of the base 1813, but the recess could instead simply be a depression in the top surface 1813*c* of the base 1813.

Figure 22:
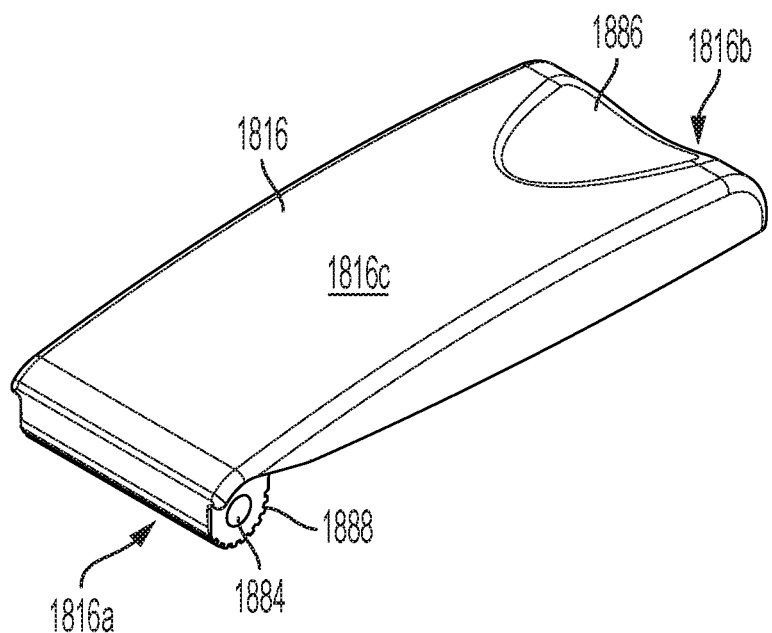
FIGS. 22 and 23 illustrate an appendage support of the device of FIGS. 18 and 19.
Figure 23:
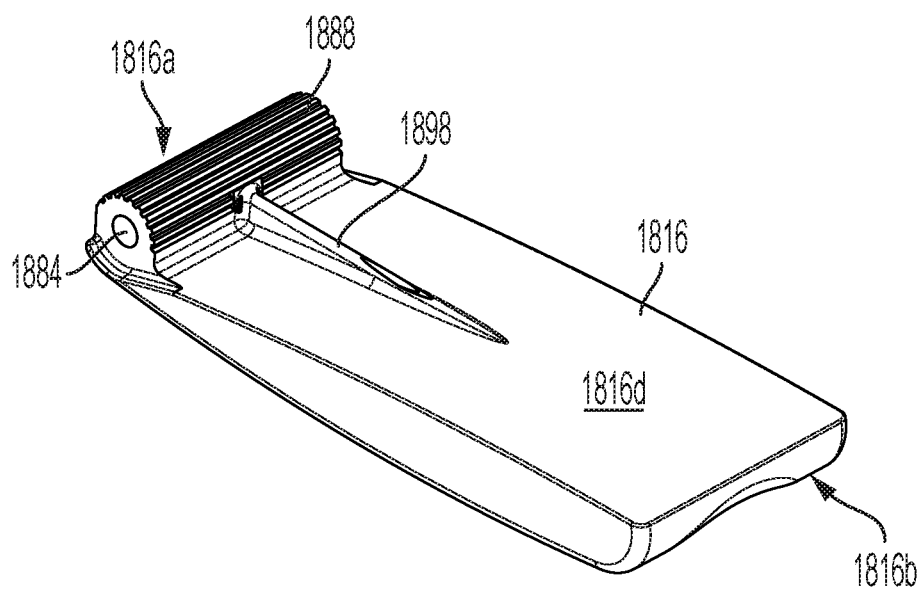
Figure 24:
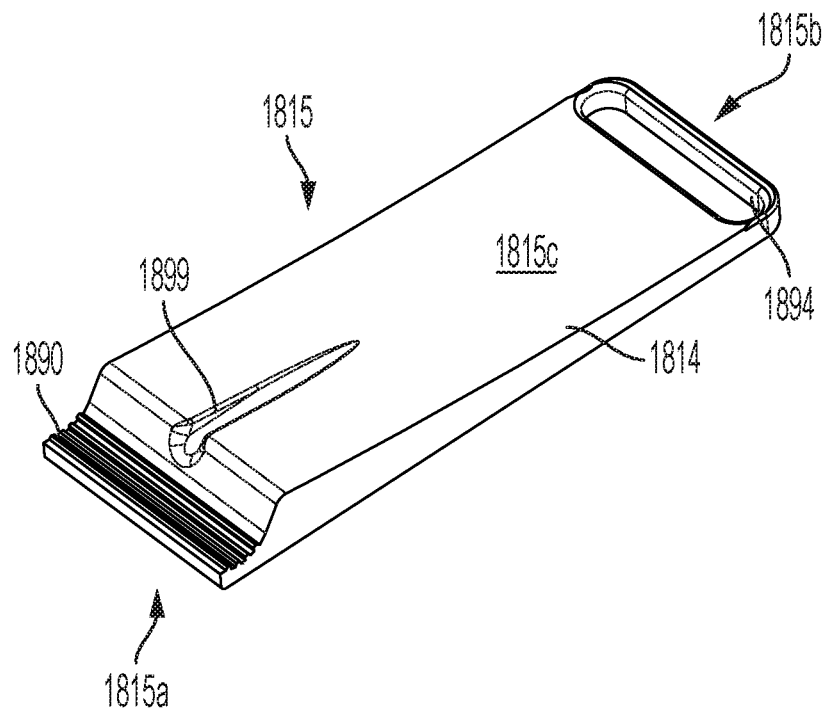
FIGS. 24 and 25 illustrate a locking arm of the device of FIGS. 18 and 19.

Referring to FIGS. 22 and 23, the appendage support 1816 is also elongated and has a first end 1816*a* and a second end 1816*b*. As shown in FIGS. 18 and 19, the first end 1816*a* of the appendage support 1816 is pivotably coupled to the base 1813 at the first end 1813*a* of the base 1813. Specifically, the first end 1816*a* (rod-receiving end) of the appendage support 1816 comprises a channel 1884 for receiving the pivot rod 1880 so as to couple the appendage support 1816 to the base 1813. The channel 1884 is shown as a closed cylinder, but could instead have a portion that is open (e.g., a slot) to allow the first end 1816*a* of the appendage support 1816 to snap around the pivot rod 1880. By way of the pivot rod 1880, the appendage support 1816 is pivotable with respect to the first and second arms 1812, 1814, and the appendage support 1816 and at least one of the first and second arms 1812, 1814 share a common pivot axis A (see FIG. 18). The first end 1816*a* of the appendage support 1816 comprises a curved, toothed portion 1888, which is generally semi-cylindrical and includes the cylindrical channel 1884 therein. The appendage support 1816 also comprises the above-noted depression 1886 on a top side 1816*c* thereof for receiving the person's extremity. A longitudinally extending fin 1898 is formed in the bottom side 1816*d* of the appendage support 1816.

A locking arm 1815 (FIGS. 24 and 25) is engageable with the appendage support 1816 and the base 1813. The locking arm 1815 comprises a wedge-shaped end 1815*a* configured to be located proximate the first end 1813*a* of the base 1813. The wedge-shaped end 1815*a* of the locking arm 1815 comprises a curved, toothed portion 1890, by way of which the wedge-shaped end 1815*a* is configured to engage with the first end 1816*a* (i.e., rod-receiving end) of the appendage support 1816. The opposite end 1815*b* of the locking arm 1815 comprises a projection 1892 on the bottom surface 1815*d* thereof and an aperture 1894, which will be described further herein below. The top surface 1815*c* of the locking arm 1815 has a channel 1899 formed therein, sized and shaped to receive the fin 1898 on the bottom side 1816*d* of the appendage support 1816 when the locking arm 1815 and the appendage support 1816 lie alongside one another.

Figure 25:
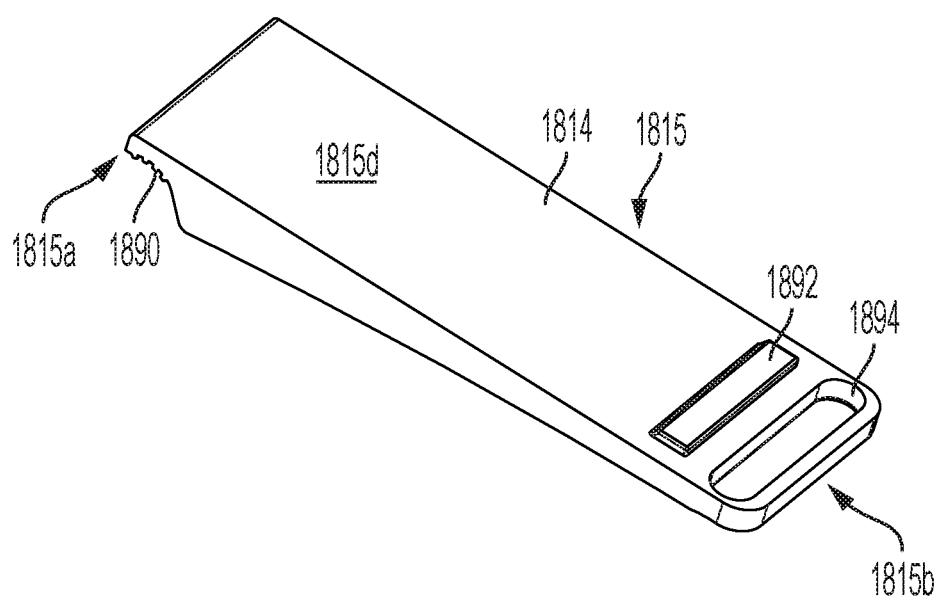

By comparison of FIGS. 20 and 25, it can be seen that the recess 1882 in the base 1813 receives the projection 1892 on the locking arm 1815 so as to secure the locking arm 1815 to the base 1813 at least in the collapsed position. Such securement can be by way of sizing of the recess 1882 and projection 1892 to create an interference or snap fit. Note that the base 1813 could instead have a projection on the top surface 1813*c* thereof, and the locking arm 1815 could have a corresponding recess. Thus, one of the first and second arms 1812, 1814 comprises a projection 1892 and the other of the first and second arms 1812, 1814 comprises a recess 1882 for receiving the projection 1892 so as to secure the first and second arms 1812, 1814 together at least in the collapsed position.

Figure 26:
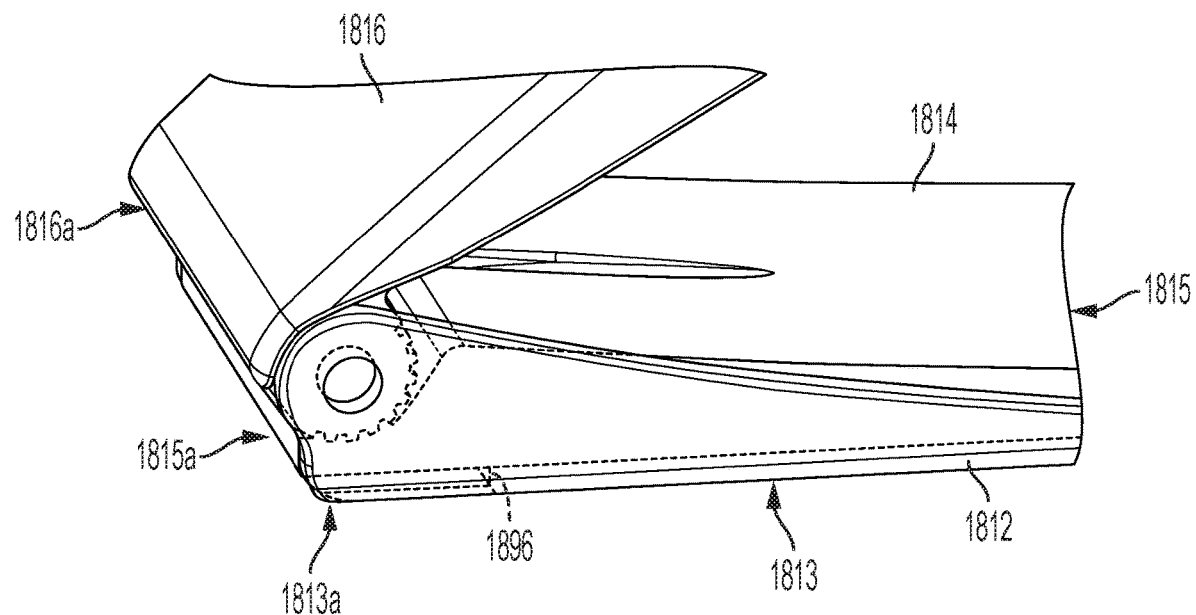
FIG. 26 illustrates a portion of the device of FIGS. 18 and 19 when the device is in a use position.
Figure 27:
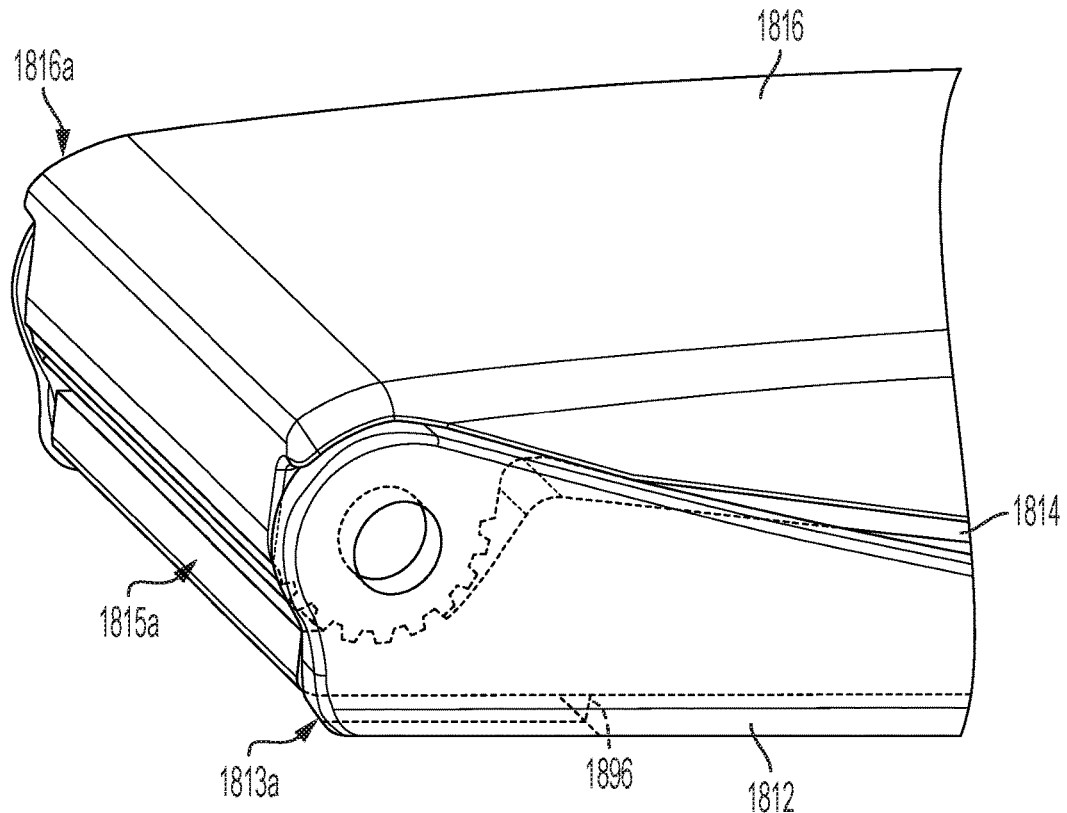
FIG. 27 illustrates a portion of the device of FIGS. 18 and 19 when the device is in a collapsed position.
Figure 28:
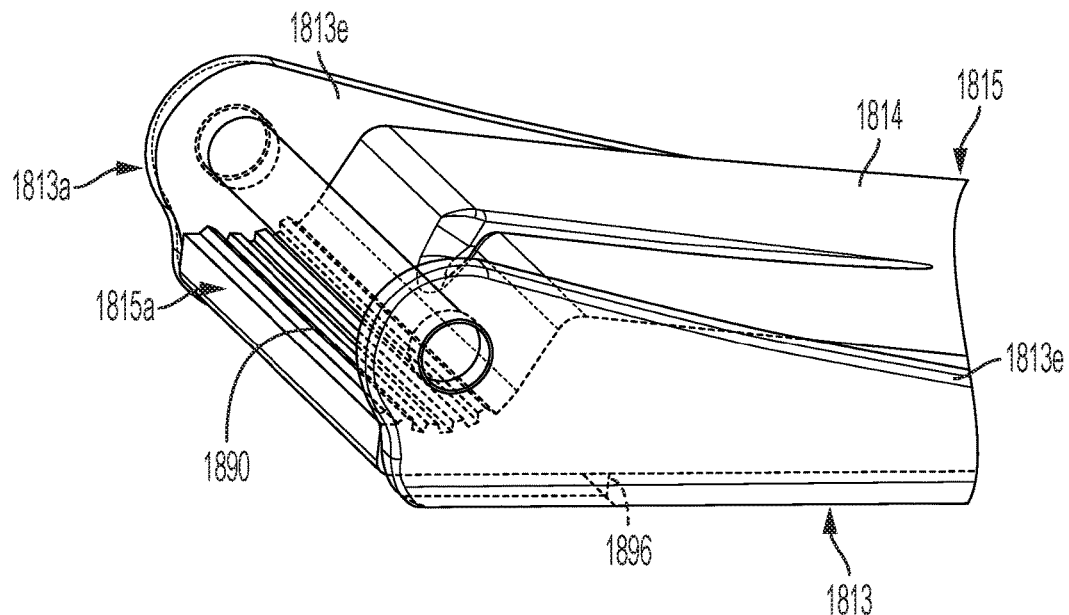
FIG. 28 illustrates a portion of the device of FIGS. 18 and 19 with the appendage support removed.

As shown in FIGS. 26-28, the first end 1816*a* (i.e., rod-receiving end) of the appendage support 1816 and the wedge-shaped end 1815*a* of the second arm 1814 comprise corresponding curved surfaces (curved, toothed portions 1890, 1888) with matable teeth for locking a position of the appendage support 1816 and the second arm 1814 with respect to one another. By way of mating of the teeth, engagement between the curved, toothed portions 1890, 1888 prevents pivoting of the appendage support 1816 with respect to the locking arm 1815. As shown in FIG. 26, when the device 1800 is in the use position, the appendage support 1816 is prevented from pivoting with respect to the base 1813 by way of engagement with the locking arm 1815. This is because, when the device 1800 is in the use position, the locking arm 1815 lies parallel to the base 1813 and the curved, toothed portions 1890, 1888 of the locking arm 1815 and the appendage support 1816 are engaged with one another.

Figure 29:
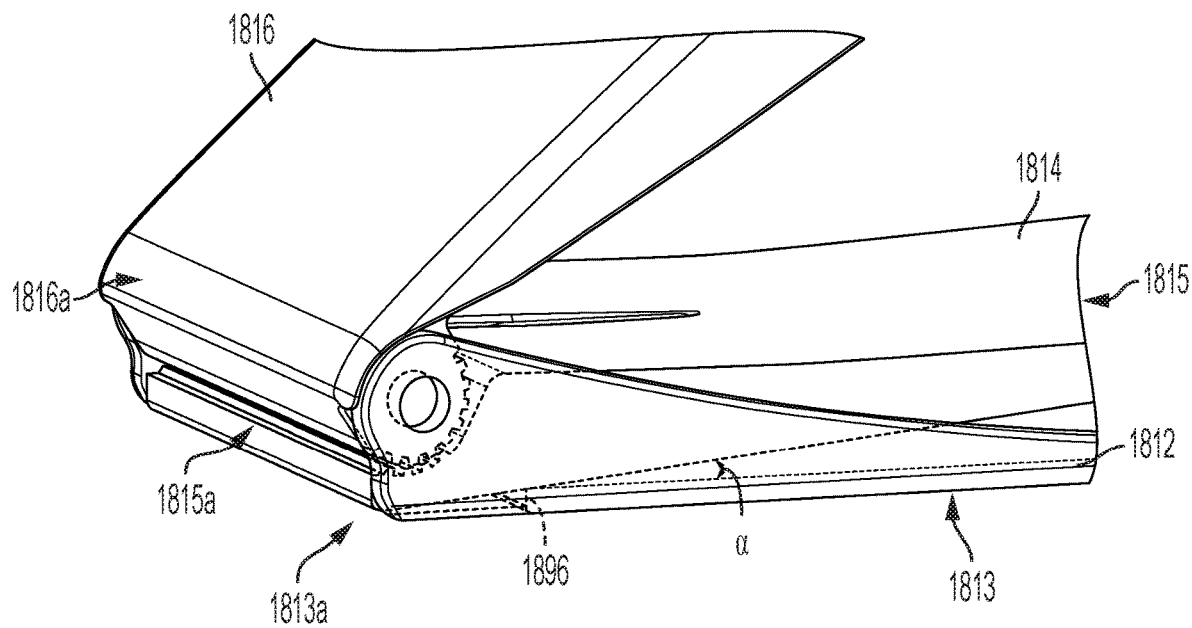
FIG. 29 illustrates a portion of the device of FIGS. 18 and 19 when the device is in an unlocked position.

However, as shown in FIG. 29, when the second arm 1814 is pivoted away from the first arm 1812 (here, by the exemplary angle α), the teeth on the wedge-shaped end 1815*a* of the second arm 1814 are not engaged with the teeth on the rod-receiving end (first end 1816*a*) of the appendage support 1816. Thus, the appendage support 1816 is freely pivotable with respect to the first and second arms 1812, 1814 about the pivot rod 1880. Such pivoting of the second arm 1814 away from the first arm 1812 is facilitated by way of the fulcrum 1896 formed in the base 1813, upon which the locking arm 1815 is pivotable so as to engage and disengage the curved, toothed portion 1890 of the locking arm 1815 with the curved, toothed portion 1888 of the appendage support 1816. As shown in FIG. 29, when the locking arm 1815 is pivoted away (upwards) from the base 1813 about the fulcrum 1896, the curved, toothed portions 1890, 1888 of the locking arm 1815 and the appendage support 1816 are not engaged with one another.

In contrast, as shown in FIGS. 26 and 27, when the second arm 1814 lies alongside and parallel to the first arm 1812, for example when the angle α=0, the teeth on the wedge-shaped end 1815a of the second arm 1814 are engaged with the teeth on the rod-receiving end (first end 1816a) of the appendage support 1816, and the appendage support 1816 is locked in place with respect to the second arm 1814. Such engagement of the toothed portions 1890, 1888 of the locking arm 1815 and the appendage support 1816 occurs when the device 1800 is in the use position shown in FIGS. 18 and 26, and thus the appendage support 1816 is prevented from pivoting downwardly while force from a person's limb resting on the top side 1816c of the appendage support 1816 is applied. Such engagement of the curved, toothed portions 1890, 1888 of the locking arm 1815 and the appendage support 1816 also occurs when the device 1800 is in the collapsed position shown in FIGS. 19 and 27, and thus the device 1800 can be transported and stored without fear that it will swing open. Engagement of the projection 1892 with the recess 1882 and of the fin 1898 with the channel 1899 by way of interference or snap fits also prevents the device 1800 from swinging open when in the collapsed position.

Starting from the collapsed position, to adjust the height of the second end 1816b of the appendage support 1816 with respect to the second end 1813b of the base 1813, the user pivots the appendage support 1816 about the pivot rod 1880 and the locking arm 1815 about the fulcrum 1896 in an upward direction. Such pivoting is allowed despite initial engagement of the curved, toothed portions 1888, 1890 because the appendage support 1816 and locking arm 1815 initially pivot together. As the locking arm 1815 continues to pivot upwardly about the fulcrum 1896, its curved, toothed portion 1890 disengages from the curved, tooth portion 1888 of the appendage support 1816. The appendage support 1816 can then be rotated to the desired height/angle. Once the desired height/angle of the appendage support 1816 is achieved, the locking arm 1815 can be pivoted back down about the fulcrum 1896 until the end 1815b thereof is adjacent the second end 1813b of the base 1813, which simultaneously raises the wedge-shaped end 1815a and mates the teeth of the curved, toothed portions 1888, 1890. Further pivoting of the appendage support 1816 is thereby prevented while the locking arm 1815 lies parallel to the base 1813. Referring back to FIG. 18, as such, the device 1800 is configurable in the use position, in which the second end 1816b of the appendage support 1816 is located a first distance or height from the second end 1813b of the base 1813. If the user desires to further adjust the height of the appendage support 1816, the user can lift the end 1815b of the locking arm 1815 until the teeth on the curved, toothed portions 1888, 1890 are no longer engaged, and thereafter pivot the appendage support 1816 about the pivot rod 1880. Once the new desired height of the appendage support 1816 is achieved, the user may rotate the end 1815b of the locking arm 1815 back down toward the base 1813 to again lock the curved, toothed portions 1888, 1890 together.

To collapse the device 1800, the user may use the aperture 1894 as a handle to lift the end 1815b of the locking arm 1815 until the teeth on the curved, toothed portions 1888, 1890 are no longer engaged, and thereafter pivot the appendage support 1816 about the pivot rod 1880 in a downward direction until the fin 1898 on the appendage support 1816 and the channel 1899 on the locking arm 1815 engage. The locking arm 1815 and appendage support 1816 can then be pivoted together toward the base 1813, until the projection 1892 is received in the recess 1882. Thus, the device 1800 is also configurable in the collapsed position, shown in FIG. 19, in which the second end 1816b of the appendage support 1816 is located at a second, shorter distance or height from the second end 1813b of the base 1813, and the locking arm 1815 is sandwiched between the base 1813 and the appendage support 1816.

Note that the first, greater distance or height of the second end 1816b of the appendage support 1816 with respect to the second end 1813b of the base 1813 can be other than that shown herein in FIG. 18, and the appendage support 1816 can be pivoted about the pivot rod 1880 to various angles with respect to the base 1813 as shown by the arrow P.

In the above example of FIGS. 18-29 (and in the examples about to be described below), the appendage support 1816 is made at least in part of a resilient material, such as rubber/elastomer, foam, or soft plastic, to provide comfort to the person's extremity resting thereupon. The appendage support 1816 may include a more rigid inner structure with a softer and/or less rigid outer covering. In the above example and the examples described herein below, the base 1813 and the locking arm 1815 can be made of rigid plastic or lightweight metal.

Figure 30:
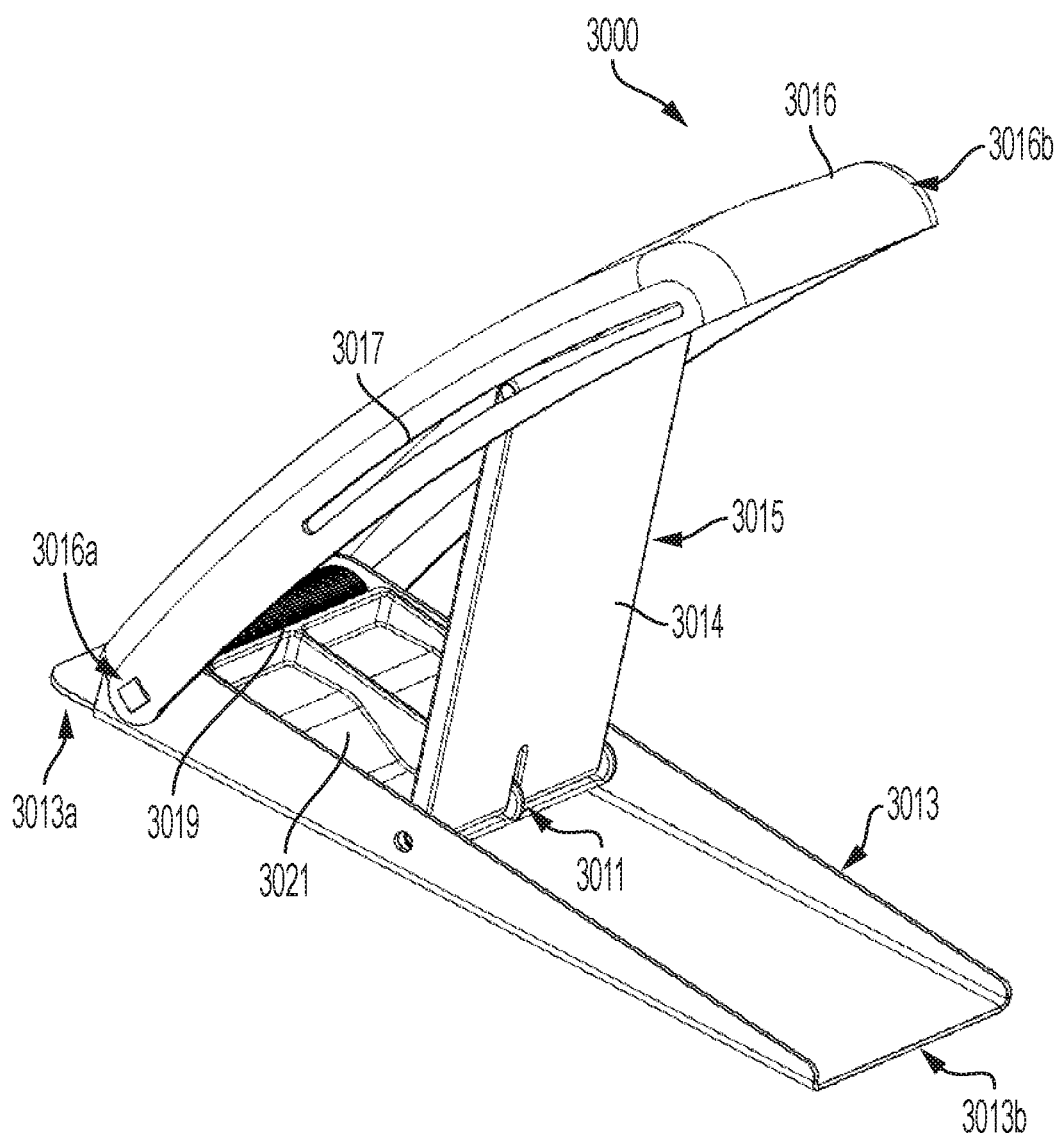
FIGS. 30-34 illustrate various other embodiments of a device for supporting a person's extremities according to the present disclosure.

FIG. 30 shows an alternative embodiment of a device 3000 including an elongated base 3013 having a first end 3013a and a second end 3013b. An elongated appendage support 3016 has a first end 3016a and a second end 3016b, the first end 3016a of the appendage support 3016 being pivotably coupled to the base 3013 at the first end 3013a of the base 3013. A locking arm 3015 is engageable with the appendage support 3016 and the base 3013. Here, the locking arm 3015 comprises first and second plates 3014, 3021 that are pivotably coupled to the base 3013 at 3011. The opposite end of the first plate 3014 has pins on either side that slide in slots 3017 in sidewalls of the appendage support 3016. A pawl mechanism 3019 located around the pivot axis of the appendage support 3016 engages with the opposite end of second locking arm plate 3021 to prevent free pivoting of the appendage support 3016 with respect to the base 3013. The device 3000 is configurable in a use position, in which the second end 3016b of the appendage support 3016 is located a first distance from the second end 3013b of the base 3013, and the appendage support 3016 is prevented from pivoting with respect to the base 3013 by way of engagement with the locking arm 3015. The device 3000 is also configurable in a collapsed position, in which the second end 3016b of the appendage support 3016 is located at a second, shorter distance from the second end 3013b of the base 3013, and the locking arm 3015 is sandwiched between the base 3013 and the appendage support 3016.

Figure 31:
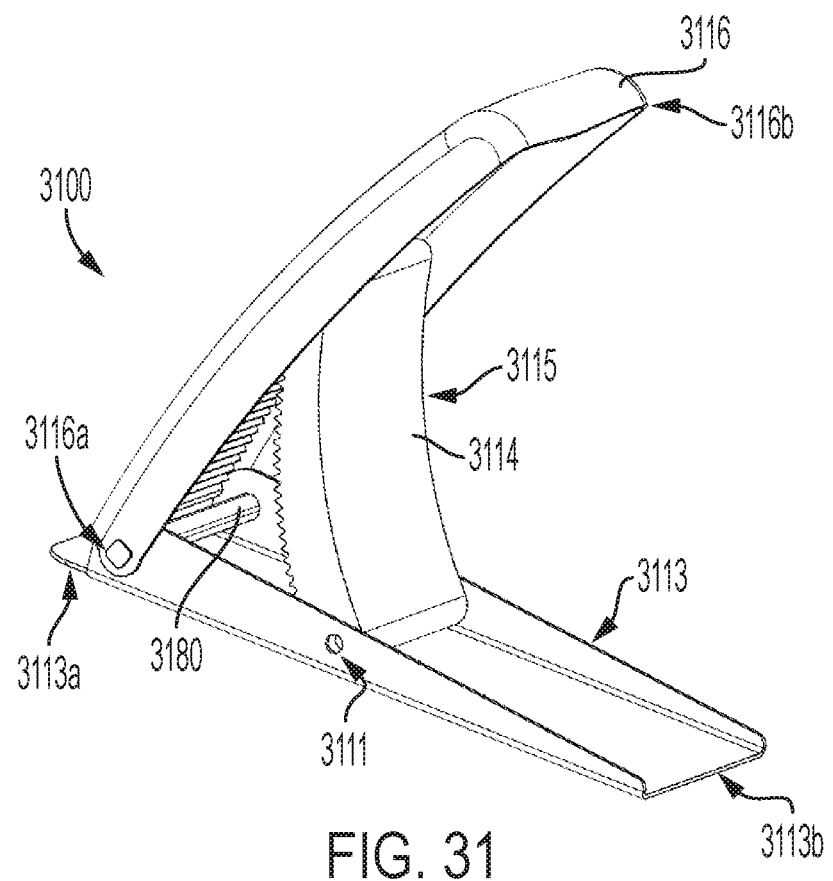

FIG. 31 shows an alternative embodiment of a device 3100 including an elongated base 3113 having a first end 3113a and a second end 3113b. An elongated appendage support 3116 has a first end 3116a and a second end 3116b, the first end 3116a of the appendage support 3116 being pivotably coupled to the base 3113 at the first end 3113a of the base 3113 by a pivot rod 3180. A locking arm 3115 is engageable with the appendage support 3116 and the base 3113. Here, the locking arm 3115 comprises a curved plate 3114 that is pivotably coupled at a first end to the base 3113 at 3111. One face of the locking arm 3115 has teeth that engage with teeth on an underside of the appendage support 3116 to prevent free pivoting of the appendage support 3116 with respect to the base 3113. The device 3100 is configurable in a use position, in which the second end 3116b of the appendage support 3116 is located a first distance from the second end 3113b of the base 3113, and the appendage support 3116 is prevented from pivoting with respect to the base 3113 by way of engagement with the locking arm 3115. The device 3100 is also configurable in a collapsed position, in which the second end 3116b of the appendage support 3116 is located at a second, shorter distance from the second end 3113b of the base 3113, and the locking arm 3115 is sandwiched between the base 3113 and the appendage support 3116.

Figure 32:
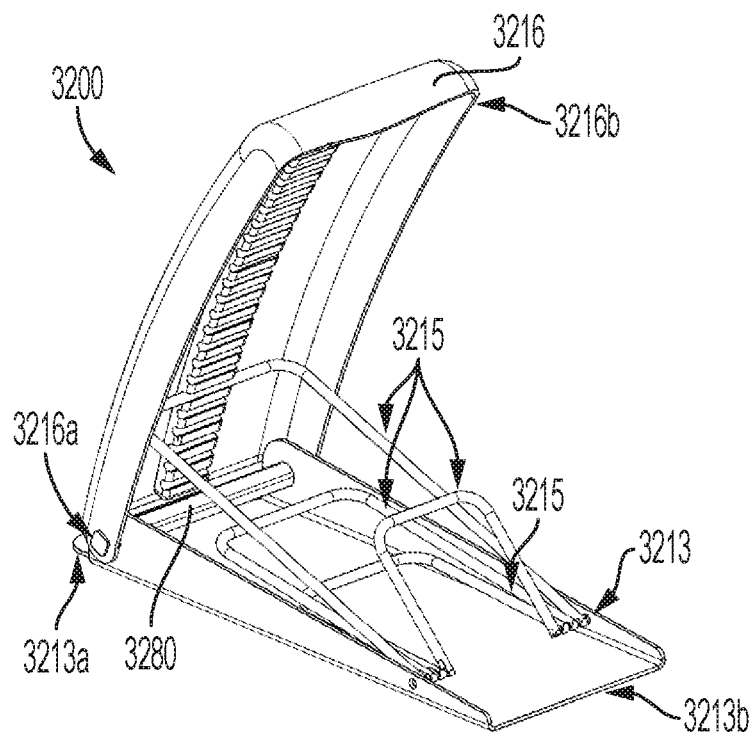

FIG. 32 shows an alternative embodiment of a device 3200 including an elongated base 3213 having a first end 3213a and a second end 3213b. An elongated appendage support 3216 has a first end 3216a and a second end 3216b, the first end 3216a of the appendage support 3216 being pivotably coupled to the base 3213 at the first end 3213a of the base 3213 by a pivot rod 3280. A plurality of locking arms 3215 are engageable with the appendage support 3216 and the base 3213. Here, the locking arms 3215 comprises tabs that are pivotably coupled at first ends to the base 3213. The other ends of the tabs engage with teeth or slots on an underside of the appendage support 3216 to prevent free pivoting of the appendage support 3216 with respect to the base 3213. The device 3200 is configurable in a use position, in which the second end 3216b of the appendage support 3216 is located a first distance from the second end 3213b of the base 3213, and the appendage support 3216 is prevented from pivoting with respect to the base 3213 by way of engagement with one of the locking arms 3215. Note that different angles/heights of the appendage support 3216 are capable of being achieved due to the different sizes of tabs as well as the provision of teeth/slots along the majority of the underside of the appendage support 3216. The device 3200 is also configurable in a collapsed position, in which the second end 3216b of the appendage support 3216 is located at a second, shorter distance from the second end 3213b of the base 3213, and the locking arms 3215 are sandwiched between the base 3213 and the appendage support 3216.

Figure 33:
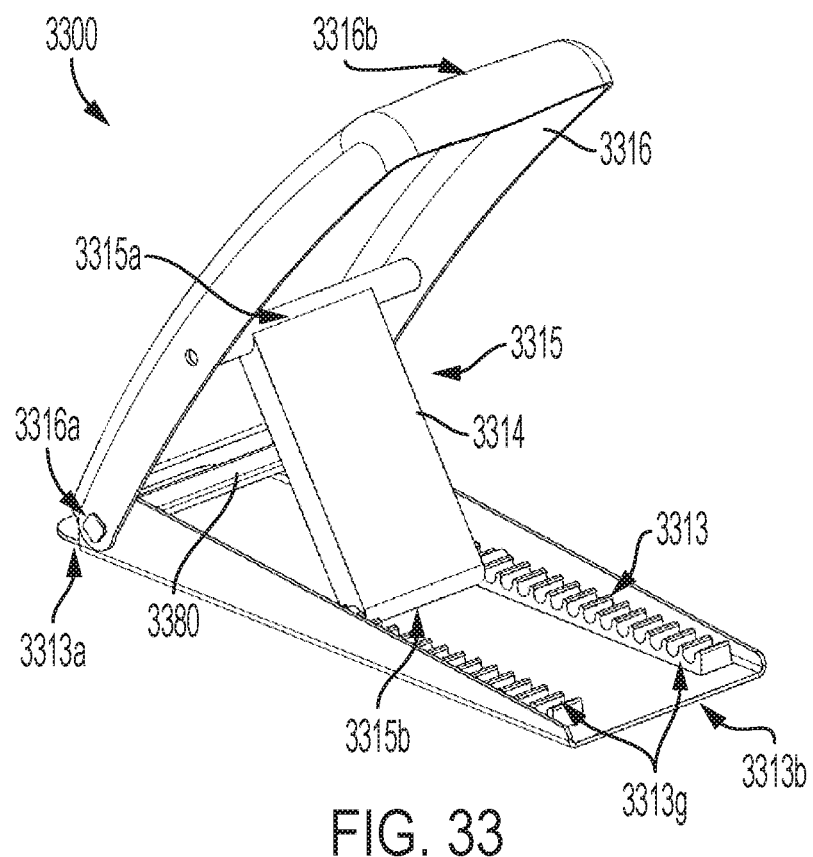

FIG. 33 shows an alternative embodiment of a device 3300 including an elongated base 3313 having a first end 3313a and a second end 3313b. An elongated appendage support 3316 has a first end 3316a and a second end 3316b, the first end 3316a of the appendage support 3316 being pivotably coupled to the base 3313 at the first end 3313a of the base 3313 by a pivot rod 3380. A locking arm 3315 is engageable with the appendage support 3316 and the base 3313. Here, the locking arm 3315 comprises an arm 3314 that is pivotably coupled at the first end 3313a thereof to the underside of the appendage support 3316. The other end 3315b of the arm 3314 is connectable by way of pins projecting from either side thereof to any slot in a series of locking slots 3313g in the base 3313. The device 3300 is configurable in a use position, in which the second end 3316b of the appendage support 3316 is located a first distance from the second end 3313b of the base 3313, and the appendage support 3316 is prevented from pivoting with respect to the base 3313 by way of engagement between the locking arm 3315 with one of the locking slots 3313g. Note that different heights of the appendage support 3316 are capable of being achieved due to the different locations of the locking slots 3313g along the length of the base 3313. The device 3300 is also configurable in a collapsed position, in which the second end 3316b of the appendage support 3316 is located at a second, shorter distance from the second end 3313b of the base 3313, and the locking arm 3415 is sandwiched between the base 3313 and the appendage support 3316.

Figure 34:
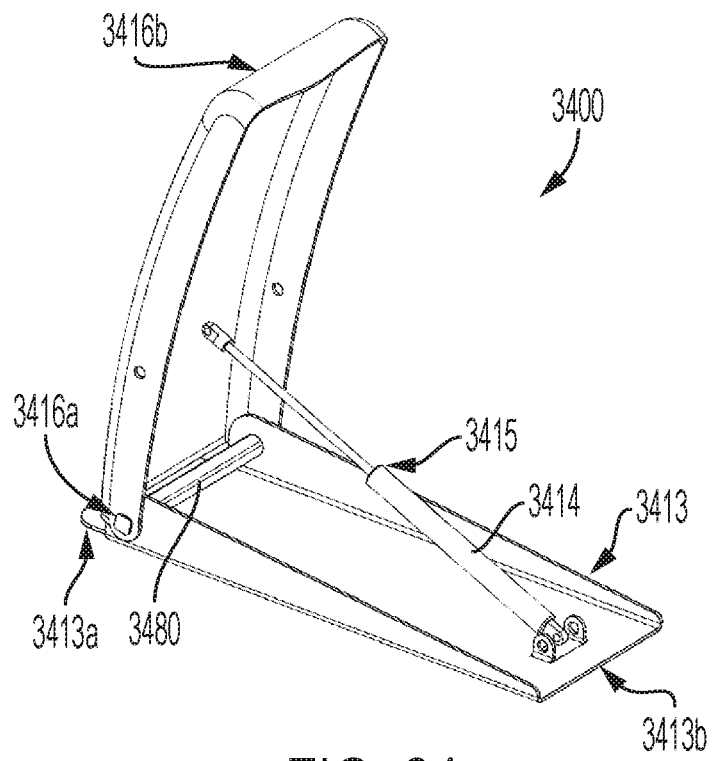

FIG. 34 shows an alternative embodiment of a device 3400 including an elongated base 3413 having a first end 3413a and a second end 3413b. An elongated appendage support 3416 has a first end 3416a and a second end 3416b, the first end 3416a of the appendage support 3416 being pivotably coupled to the base 3413 at the first end 3413a of the base 3413 by a pivot rod 3480. A locking arm 3415 is coupled between the appendage support 3416 and the base 3413. Here, the locking arm 3415 comprises a piston-cylinder 3414 that is pivotably coupled at one end thereof to the appendage support 3416 and at the other end thereof to the base 3413. The piston-cylinder 3414 provides damped pivoting of the appendage support 3416 away from the base 3413, and a valve inside the piston-cylinder 3414 can be closed to prevent pivoting of the appendage support 3416 down towards the base 3413. The device 3400 is configurable in a use position, in which the second end 3416b of the appendage support 3416 is located a first distance from the second end 3413b of the base 3413, and the appendage support 3416 is prevented from pivoting with respect to the base 3413 by way of closing the valve in the piston-cylinder 3414. By opening the valve and allowing the piston rod to retract into the cylinder, the device 3400 is also configurable in a collapsed position, in which the second end 3416b of the appendage support 3416 is located at a second, shorter distance from the second end 3413b of the base 3413, and the locking arm 3415 is sandwiched between the base 3413 and the appendage support 3416.

In the above description, certain terms have been used for brevity, clarity, and understanding. No unnecessary limitations are to be inferred therefrom beyond the requirement of the prior art because such terms are used for descriptive purposes and are intended to be broadly construed. The different devices described herein may be used alone or in combination with other assemblies and devices. It is to be expected that various equivalents, alternatives and modifications are possible within the scope of the appended claims.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A device for supporting a person's extremities, the device comprising:
    an elongated base having a first end and a second end;
    an elongated appendage support having a first end and a second end, the first end of the appendage support being pivotably coupled to the base at the first end of the base; and
    a locking arm engageable with the appendage support and the base;

wherein the device is configurable in a use position, in which the second end of the appendage support is located a first distance from the second end of the base, and the appendage support is prevented from pivoting with respect to the base by way of engagement with the locking arm; and wherein the device is configurable in a collapsed position, in which the second end of the appendage support is located at a second, shorter distance from the second end of the base, and the locking arm is sandwiched between the base and the appendage support.

2. The device of claim 1, wherein the locking arm comprises a wedge-shaped end proximate the first end of the base.

3. The device of claim 2, wherein the wedge-shaped end of the locking arm comprises a curved, toothed portion, and the first end of the appendage support comprises a corresponding curved, toothed portion, wherein engagement between the curved, toothed portions prevents pivoting of the appendage support with respect to the locking arm.

4. The device of claim 3, wherein the base comprises a fulcrum upon which the locking arm is pivotable so as to engage and disengage the curved, toothed portion of the locking arm with the curved, toothed portion of the appendage support.

5. The device of claim 4, wherein in the use position, the locking arm lies parallel to the base, and the curved, toothed portions of the locking arm and the appendage support are engaged with one another.

6. The device of claim 4, wherein when the locking arm is pivoted away from the base, the curved, toothed portions of the locking arm and the appendage support are not engaged with one another.

7. The device of claim 1, further comprising a pivot rod coupled to the first end of the base, wherein the first end of the appendage support comprises a channel for receiving the pivot rod so as to couple the appendage support to the base.

8. The device of claim 1, wherein the locking arm comprises a projection and the base comprises a recess for receiving the projection so as to secure the locking arm to the base at least in the collapsed position.

9. The device of claim 1, wherein the appendage support comprises a depression for receiving the person's extremity.

10. The device of claim 1, wherein when the device is in the use position, the base is configured to rest on a generally horizontal support surface, and the appendage support is configured to extend upwardly away from the generally horizontal support surface.

* * * * *